(12) United States Patent
Sevrain et al.

(10) Patent No.: US 7,850,983 B2
(45) Date of Patent: Dec. 14, 2010

(54) METHODS AND COMPOSITIONS FOR REPAIR OF CARTILAGE USING AN IN VIVO BIOREACTOR

(75) Inventors: Lionel C. Sevrain, West Palm Beach, FL (US); Sylvie Y. Verdier-Sevrain, West Palm Beach, FL (US)

(73) Assignee: Spinalcyte, LLC, Houston, TX (US)

( * ) Notice: Subject to any disclaimer, the term of this patent is extended or adjusted under 35 U.S.C. 154(b) by 811 days.

(21) Appl. No.: 11/671,082

(22) Filed: Feb. 5, 2007

(65) Prior Publication Data

US 2007/0184033 A1    Aug. 9, 2007

Related U.S. Application Data

(60) Provisional application No. 60/785,478, filed on Mar. 24, 2006, provisional application No. 60/771,172, filed on Feb. 7, 2006.

(51) Int. Cl.
A61F 2/30 (2006.01)
A61F 13/00 (2006.01)
A61K 9/50 (2006.01)

(52) U.S. Cl. ...................................... 424/400; 424/422
(58) Field of Classification Search ................. 424/400, 424/422
See application file for complete search history.

(56) References Cited

U.S. PATENT DOCUMENTS

| 5,736,372 | A  | 4/1998  | Vacanti et al.   |
|-----------|----|---------|------------------|
| 6,489,165 | B2 | 12/2002 | Bhatnagar et al. |
| 6,530,956 | B1 | 3/2003  | Mansmann         |
| 6,627,422 | B1 | 9/2003  | Li et al.        |
| 6,916,640 | B2 | 7/2005  | Yu et al.        |
| 2002/0029083 | A1 | 3/2002 | Zucherman et al. |
| 2002/0094569 | A1 | 7/2002 | Yu et al.        |
| 2002/0106625 | A1 | 8/2002 | Hung et al.      |
| 2003/0229400 | A1 | 12/2003 | Masuda et al.   |
| 2005/0090901 | A1 | 4/2005 | Studer           |
| 2006/0019362 | A1 | 1/2006 | Yu et al.        |
| 2006/0147486 | A1 | 7/2006 | Kim et al.       |

FOREIGN PATENT DOCUMENTS

| WO | WO-9632076    | 10/1996 |
| WO | WO-2004078954 | 9/2004  |
| WO | WO-2006011855 | 2/2006  |

OTHER PUBLICATIONS

Bartkowiak et al., "Alginate-Oligochitosan Microcapsules: A Mechanistic Study Relating Membrane and Capsule Properties to Reaction Conditions", Chem. Mater., 1999, 2486-2492, vol. 11 (9).
Botchwey et al., "Tissue engineered bone: Measurement of nutrient transport in three-dimensional matrices", Journal of Biomedical Materials Research Part A, Published Online: 2003, 357-367, vol. 67A(1).
Chia et al., "Hepatocyte Encapsulation for Enhanced Cellular Functions", Tissue Engineering, 2000, 481-495; 6(5).
Endres et al., "Osteogenic Induction of Human Bone Marrow-Derived Mesenchymal Progenitor Cells in Novel Synthetic Polymer-Hydrogel Matrices", Tissue Engineering, 2003, 689-702; vol. 9(4).
Exploit Technologies Private Limited, "Macroencapsulation of Cells in 3D Scaffolds by Polyelectrolyte Complex Coacervation".
Kim et al., "Optimizing seeding and culture methods to engineer smooth muscle tissue on biodegradable polymer matrices", Biotechnology and Bioengineering, 46-54, Published Online: 2000, 46-54; vol. 57(1).
Li et al., "Effects of Filtration Seeding on Cell Density, Spatial Distribution, and Proliferation in Nonwoven Fibrous Matrices", Biotechnol. Prog., 2001, 935-944, vol. 17(5).
Moran et al., "Characterization of polylactic acid-polyglycolic acid composites for cartilage tissue engineering", Tissue Eng., 2003, 63-70, vol. 9(1).
U.S. Appl. No. 10/899,899, filed Jan. 26, 2006, Yu et al.
Renken et al., "Microencapsulation: A review of polymers and technologies with a focus on bioartificial organs", Polimery, 1998, 530-539, vol. 43(9).
Ringe et al., "Stem cells for regenerative medicine: advances in the engineering of tissues and organs", Naturwissenschaften, 2002, Epub 2002, 23338-51, vol. 89(8).
Roberts et al., "Dopamine secretion by PC12 cells microencapsulated in a hydroxyethyl methacrylate-methyl methacrylate copolymer", Biomaterials, 1996, 267-275, vol. 17(3).
Schantz et al., "Repair of Calvarial Defects with Customized Tissue-Engineered Bone Grafts I. Evaluation of Osteogenesis in a Three-Dimensional Culture System", Tissue Engineering, 2003, 113-126, 9(supplement 1).
Shao, et al., "Microcapsules through polymer complexation I: Complex coacervation of polymers containing a high charge density", Biomaterials, 1991, 374-384; vol. 12.
Sittinger et al., "Artificial tissues in perfusion culture", Int. J. Artif. Organs, 1997, 57-62, vol. 20(1).
Sittinger et al., "Encapsulation of artificial tissues in polyelectrolyte complexes: preliminary studies", Biomaterials, 1996, 1049-1051(3), vol. 17(10).
Toh et al., "A Configurable Three-Dimensional Microenvironment in a Microfluidic Channel for Primary Hepatocyte Culture", ASSAY and Drug Development Technologies. 2005, 169-176, vol. 3(2).

(Continued)

*Primary Examiner*—Ruth A Davis
(74) *Attorney, Agent, or Firm*—Fulbright & Jaworski, L.L.P.

(57) ABSTRACT

Methods and compositions for the biological repair of cartilage using a hybrid construct combining both an inert structure and living core are described. The inert structure is intended to act not only as a delivery system to feed and grow a living, core component, but also as an inducer of cell differentiation. The inert structure comprises concentric internal and external and inflatable/expandable balloon-like bio-polymers. The living core comprises the cell-matrix construct comprised of HDFs, for example, seeded in a scaffold. The method comprises surgically removing a damaged cartilage from a patient and inserting the hybrid construct into the cavity generated after the foregoing surgical intervention. The balloons of the inert structure are successively inflated within the target area, such as a joint, for example. Also disclosed herein are methods for growing and differentiating human fibroblasts into chondrocyte-like cells via mechanical strain.

52 Claims, 4 Drawing Sheets

OTHER PUBLICATIONS

Uludag et al., "Technology of mammalian cell encapsulation", Advanced Drug Delivery Reviews, 2000, 29-64(36), vol. 42(1).

Ushida et al., "Three-Dimensional Seeding of Chondrocytes Encapsulated in Collagen Gel Into PLLA Scaffolds", Cell Transplantation, 2002, 489-494(6), vol. 11(5).

Wallace et al., "Collagen gel systems for sustained delivery and tissue engineering", Advanced Drug Delivery Reviews, 2003, 1631-1649(19), vol. 55(12).

Wen et al., "Microcapsules through polymer complexation—Part 3: encapsulation and culture of human Burkitt lymphoma cells in vitro", Biomaterials, 1995, 325-335(11), vol. 16(4).

Wendt et al., "Oscillating perfusion of cell suspensions through three-dimensional scaffolds enhances cell seeding efficiency and uniformity", Biotechnology and Bioengineering <http://www3.interscience.wiley.com/journal/71002188/home>, Published Online: 2003, 205-214, vol. 84(2).

Yang et al., "Novel cell immobilization method utilizing centrifugal force to achieve high-density hepatocyte culture in porous scaffold", Journal of Biomedical Materials Research, 379-386, Published Online: 2001, vol. 55(3).

International Search Report issued Feb. 18, 2009, during the prosecution of International Application No. PCT/US2007/061590.

Written Opinion issued Feb. 18, 2009, during the prosecution of International Application No. PCT/US2007/061590. Published Feb. 27, 2009.

International Preliminary Report on Patentability issued Mar. 3, 2009, during the prosecution of International Application No. PCT/US2007/061590. Published Mar. 3, 2009.

Toh et al., "Application of a polyelectrolyte complex coacervation method to improve seeding efficiency of bone marrow stromal cells in a 3D culture system", Biomaterials, Jul. 2005; 26(19):4149-60.

First Office Action, issued Jul. 13, 2010 (published Jul. 13, 2010) during the prosecution of Chinese Application No. 20078004506.8.

Examiner's First Report, issued Aug. 11, 2010 (published Aug. 11, 2010) during the prosecution of Australian Application No. 2007212085.

METHODS AND COMPOSITIONS FOR REPAIR OF CARTILAGE USING AN IN VIVO BIOREACTOR

CROSS-REFERENCE TO RELATED APPLICATIONS

The present application claims priority to U.S. Provisional Application Ser. No. 60/771,172, entitled Method for Repairing an Intervertebral Disc, and filed on Feb. 7, 2006 and also claims priority to U.S. Provisional Application Ser. No. 60/785,478, entitled Multi-Layered Multi-Compartmental Three-Dimensional Polymeric Scaffold For Intervertebral Disc Repair, and filed on Mar. 24, 2006, both of which are incorporated by reference herein in their entirety.

FIELD OF THE INVENTION

The present invention generally concerns at least the fields of medicine, surgery, anatomy, biology, cell biology, and/or molecular biology. In particular aspects, the present invention concerns the fields of cartilage repair, such as articular cartilage repair. More particularly, the field of the invention concerns cell-matrix encapsulation devices for growing, proliferating, and/or differentiating cells into chondrocyte-like cells under mechanical stress.

BACKGROUND OF THE INVENTION

Typically, articular cartilage is a tissue that is not naturally regenerated once damaged. Recently, efforts have been made to reconstruct damaged biological tissues by regenerating a portion of the damaged tissues in laboratories. This approach, defined as "tissue engineering" has raised tremendous attention.

Tissue engineering involves the development of biocompatible materials capable of specifically interacting with biological tissues to produce functional tissue equivalents. Tissue engineering has a basic concept of collecting a desired tissue from a patient, isolating cells from the tissue specimen, proliferating cells, seeding the proliferated cells onto a biodegradable polymeric scaffold, culturing the cells for a predetermined period in vitro, and transplanting back the cell/polymer construct into the patient. After transplantation, the cells in the transplanted scaffold use oxygen and nutrients gained by diffusion of body fluids to proliferate and differentiate to form a new tissue, whereas the scaffold has been dissolved.

The scaffold used for the regeneration of biological tissue is usually comprised of a material that serves as matrix to allow cells to attach to the surface of the material and form a three dimensional tissue. This material should be non-toxic, biocompatible and biodegradable. The most widely used biodegradable polymers, satisfying the aforementioned physical requirements, include organic polymers such as polyglycolic acid (PGA), polylactic-co-glycolic acid (PLGA), poly-ε-caprolactone (PCL), polyamino acids, polyanhydrides, polyorthoesters; natural hydrogels such as collagen, hyaluronic acid, alginate, agarose, chitosan; synthetic hydrogels such as poly(ethylene oxide) (PEO), poly(vinyl alcohol) (PVA), poly (acrylic acid) (PAA), poly(propylene fumarate-co-ethylene glycol) [P(PF-co-EG) and copolymers thereof.

The aforementioned polymers have been researched to fabricate porous scaffold. However, conventional fabrication techniques generally result in scaffolds with low porosities that do not adequately support cell growth. The pores on the surface of the scaffold are often blocked, nutrients are not sufficiently supplied to the cells, and cells have difficulties in growing into the scaffold. Recently, the application of microfabrication technology in the field of tissue engineering has rendered possible the development of complex scaffold with micron-scale resolution. These scaffolds referred to as "microfluidic scaffolds" present a network of micro-channels that allow fluid flow within the scaffold. This network of micro-channels helps to provide both nutrients and soluble factors to distinct sections of the scaffold.

The scaffold can also be encapsulated with a semi-permeable membrane. U.S. Patent Publication No. 2006/0147486 relates to a porous scaffold enveloped with a semi-permeable membrane. This semi-permeable membrane selectively introduces nutrients into the scaffold from outside the scaffold, as well excreting metabolic wastes generated by the tissue cells to the outside of the scaffold. The publication describes the method to grow cells within this scaffold in vitro for regenerating a biological tissue.

U.S. Pat. No. 6,627,422 describes a device containing cells in a yarn matrix encapsulated in a semi-permeable membrane. In this case, the semi-permeable membrane allows implanted cells to receive nutrients but also allows therapeutic molecules produced by the implanted cells to diffuse to host cells. This device is used for cell therapy: the encapsulated cells secrete endogenous proteins to the host. This device functions, as a bioartificial organ (for example, as artificial pancreas by secreting insulin).

Despite such progress in the engineering of scaffolds with improved diffusion of nutrients, the scaffold once transplanted to the patient suffers from a limited supply of nutrients. Indeed, in vivo, nutrients and oxygen are delivered to disc cells through blood vessels in the endplates of the vertebrae adjacent to the disc. In degenerative disc disease, the vertebral endplates of vertebrae are not well-functioning and do not allow sufficient diffusion of nutrition to the implanted cell-scaffold.

Different cell types can be used to engineer articular cartilage. Primary differentiated cells of articular cartilage (i.e. chondrocytes) from biopsies of existing cartilage can be used. These cells are often procured from an autologous source since the procurement of heterologous cells or cells from cadavers carries the inherent risk of transfer of pathogens. Mesenchymal Stem Cells (MSCs), which are embryonic-like cells found in bone marrow, are capable of differentiation into different type of mesenchymal tissues and especially cartilaginous tissue; therefore, they are another cell source for cartilage engineering.

However, these cell sourcings raise many issues. Chondrocytes from intervertebral disc are difficult to harvest, because the autologous cells are obtained from the patient's disc and therefore it requires an invasive procedure (back surgery) to perform a biopsy. If cells are harvested from a healthy disc, it jeopardizes the functioning of the healthy disc. If cells are harvested from a damaged disc during the discectomy, it provides abnormal cells from a degenerated tissue. Moreover, chondrocytes are difficult to expand in culture since they de-differentiate. Regarding chondrocytes from other cartilages, the elastic cartilage from the ear is easy to harvest, but it produces only hyaline cartilage and not fibro-cartilage, as in the disc. MSCs also have some disadvantages, because they require a bone marrow biopsy. While a large quantity of cells is needed for tissue engineering, it is difficult to obtain a large quantity of adult stem cells.

Numerous papers have reported the culture conditions that stimulate chondrogenesis of mesenchymal stem cells or de-differentiate chondrocytes. These conditions are the following: high density micromass culture; hypoxia; supplementation with growth factors, such as Bone Morphogenetic Proteins (BMP) particularly BMP-2, -4, -6, and -7, transforming growth factor beta (TGF-β), and/or insulin growth factor one (IGF-I); supplementation with ascorbic acid; culture on specific matrix, such as alginate; culture under mechanical stress such as Intermittent Hydrostatic Pressure (IHP) (Watt, 1988; Dozin et al., 1992; Sullivan et al., 1994; Denker et al., 1999; Zur Nieden et al., 2005; Zhou et al., 2004; Majumdar et al., 2001; Barry et al., 2001; Elder et al., 2005; Mow et al., 1992; Domm et al., 2000).

Few studies have reported the conversion of Human Dermal Fibroblasts (HDFs) into chondrocyte-like cells. U.S. Pat. No. 6,489,165 concerns the conversion of HDFs into chondrocyte-like cells under high density micromass culture and hypoxia. French M M et al. (2004) reported the conversion of HDFs into chondrocyte when the cells are grown on the proteoglycan, aggrecan, and supplemented with insulin growth factor one (IGF-I).

Degenerative Disc Disease

Degenerative Disc Disease (DDD) requires 700,000 procedures each year performed by 4,500 spine surgeons, and the majority of disc disorders occur in young patients. Therefore, it is critical to develop effective and safe strategies to treat this disease.

An intervertebral disc (IVD) is a complex structure comprising three distinctive tissues: the annulus, the nucleus, and cartilage endplates. The annulus is a well-organized, multi-layered structure of collagen fibers. The nucleus is comprised mainly of glycosaminoglycan (hydrophilic polymer). The cartilage endplates supply nutrients. The foregoing combination allows the normal disc to perform two conflicting functions: stability and flexibility.

The intervertebral disc absorbs shocks, maintains motion, and keeps stability. Similar to other cartilages, the innate repair capacity of the intervertebral disc (which acts as a joint between two vertebra) is low, because it is avascular and nutritionally supported only by passive diffusion at the endplates. Consequently, once the degenerative process is activated, it is ultimately considered to be an irreversible condition. Once damaged, the degenerated disc may bulge or extrude, and therefore needs to be removed.

Currently, the common surgical treatment for patients with chronic low back pain due to degenerative disc disease is either discectomy or spinal fusion. Discectomy is an appropriate procedure and is routinely performed to remove the degenerated nucleus through a fenestration within the annulus: it allows removal of both the extruded nucleus (herniectomy) and the degenerated remaining inter-vertebral nucleus fragments. Although this procedure is ideal for decompressing and relieving the nervous system (root or cauda equina), it is a poor operation for the spine, because it creates a potentially disabling condition that leads to a degenerative cascade that may require an additional invasive surgical procedure, like fusion or arthroplasty, for example. Discectomy brings a good short-term effect in relieving radicular pain, but it causes disc height reduction with neuro-foramen stenosis, instability of the treated level, poor result on back pain, and/or complications, such as spinal stenosis or facet pain, for example.

Spinal fusion is the most effective treatment for low back pain. It is a surgical procedure in which an entire disc is removed and the two adjacent vertebrae are united together ("fused") with the interposition of a graft (cages, bone grafts, and/or fixation devices, for example). It is indicated for patients with advanced disc degeneration. Over 200,000 spinal fusions are performed each year in the U.S. alone, but by eliminating the motion, the spinal fusion alters the biomechanical properties of the inter-vertebral disc and increases stress and strain on the discs that are adjacent to the fused disc. In fact, both discectomy and fusion worsen the condition of the affected disc, adjacent discs, and surrounding tissues (such as facet joints), leading to further degeneration.

The failure of these procedures has led to a search for the development of non-fusion technologies, such as disc or disc nucleus prosthesis, for example. Disc arthroplasty with an artificial disc is an emerging treatment for patients with disc degeneration. Its advantages are to maintain motion, decrease incidence of adjacent segment degeneration, avoid complications related to fusion, and allow early return to function. Today, two kinds of devices are marketed: the total disc replacement and the nuclear replacement, but both of them have major pitfalls. Total disc replacement is a bulky metallic prosthesis designed to replace the entire disc: annulus, nucleus and endplates. These prostheses use an invasive anterior (trans- or retro-peritoneal) approach that requires the presence of a vascular surgeon. Dislodgements, wear debris, degeneration of adjacent intervertebral discs, facet joint arthrosis, and subsidence of this type of prosthesis have been reported. The artificial nucleus substitute preserves the remaining disc tissues and their functions. Its design allows its implantation through a posterior approach, but the major limitation of such nucleus prosthesis is that it can be used only in patients in whom disc degeneration is at an early or intermediate stage, because it requires the presence of a competent natural annulus. Implant extrusion remains a primary concern. As a hydrogel-based device, it is fragile, and so does not resist the outstanding bio-mechanical constraints of the lumbar spine (shear forces). As inert materials, they may lose their mechanical properties over time, and tears and breakages have been reported. Replacing the nucleus only and leaving in place a damaged annulus generates the conditions for implant extrusion or recidivism of discal herniation.

Tissue engineering and regenerative medicine represent a new option for the treatment of DDD. A variety of approaches are used to regenerate tissues. These approaches can be categorized into three groups: 1) biomaterials, without additional cells, that are used to send signals to attract cells and promote regeneration; 2) cells alone may be used, to form a tissue; and 3) cells may be used with a biomaterial scaffold that acts as a frame for developing tissues. While Autologous Chondrocyte Transplantation (ACT) has been used for a few years to repair articular cartilage, tissue engineering for disc repair remains in its infancy. Intensive research is currently done, and animal studies have shown the feasibility of tissue-engineered intervertebral disc. More interestingly, recent pilot clinical studies have shown that ACT is an efficient treatment of herniated disc. The main disadvantage of ACT for disc repair is that it requires a disc biopsy. Therefore, there is a need for an improved method to restore disc anatomy and improve its functioning, and there thus remains a need for an improved method of cartilage repair. The present invention seeks to meet these and other objects and provides a solution to a long-felt need in the art.

SUMMARY OF THE INVENTION

The present invention concerns methods and compositions for biological repair of any kind of cartilage, including intervertebral and joint cartilage, for example. More specifically, but not exclusively, the present invention relates to methods and compositions for biological repair of cartilage using an implantable device that is a combination of an inert structure acting as an in vivo bioreactor, and a living structure comprised of chondrocytes or chondrocyte-like cells, for example, such as cells derived from the exemplary Human Dermal Fibroblasts (HDFs), in specific embodiments. More particularly, but not exclusively, the present invention relates to a hybrid construct combining both an inert structure and living core. The inert structure acts not only as a delivery system to feed and grow a living core component, but also acts as an inducer of cell differentiation, in certain aspects. In embodiments of the invention, this inert structure comprises two expandable balloon-like bio-polymers, namely, an internal membrane (like a balloon) that is enclosed within an external membrane (also like a balloon). Hence, the inert structure comprises two generally concentric inflatable membranes. The two membranes may be further defined as a first enclosed membrane that is structurally within a second enclosed membrane. In specific embodiments, the shapes may be considered to be generally spherical, generally elliptical, generally rounded, generally orbed, generally discoid, generally spheroidical, generally globule, balloon-like, and so forth. In additional specific embodiments, the shape is individual-specific and conforms to the shape and size of the remaining cavity in the joint or intervertebral disc region of the individual.

In certain aspects, the invention generates natural tissue in vitro, such as from stem cells, chondrocytes, and so forth. More particularly, but not exclusively, the present invention relates to a method for growing and differentiating Human Fibroblasts into chondrocyte-like cells, for example. The cells, which are autologous in certain embodiments, are put into a scaffold matrix made of one or more biopolymers, such as to mimic a natural matrix. The scaffold may be seeded in vitro, and in certain aspects growth factors are provided to the cells, the matrix, or both. The scaffold is put into a bioreactor, which is a system for perfusion of medium and allows application of mechanical force to the scaffold. Following delivery of the force, cells are assisted in differentiation, especially for generation of cartilage.

In specific embodiments, the invention employs differentiation of certain cells into chondrocyte-like cells. In specific embodiments, HDFs, for example, are differentiated into chondrocyte-like cells under particular culture conditions, such as hypoxia (Nicoll et al., 2001), high density micromass culture, and culture on specific matrix, such as aggrecan (French et al, 2004). In specific embodiments, factors that mimic the in vivo environment of intervertebral chondrocytes are potent stimuli for chondrogenic differentiation of HDFs, for example; such factors include the following: 1) three dimensionality; 2) low oxygen tension (<5%); and 3) mechanical stress; and 4) intermittent hydrostatic pressure. In specific embodiments, cell viability and chondrogenic differentiation of HDFs seeded in three-dimensional alginate bead cultures are determined. In another embodiment, the effects of oxygen tension on the differentiation of HDFs cultured in alginate beads are characterized. In an additional specific embodiment, the effects of hydrostatic compression on the differentiation of HDFs cultured in alginate beads are characterized.

Differentiation of cells into chondrocytes or chondrocyte-like cells may occur in any suitable manner, including differentiation in vitro prior to implantation of the device into an individual or differentiation in vitro prior to implantation of the device into an individual and also in vivo following implantation.

In specific embodiments the device of the invention provides a method for in vivo regeneration of a joint, such as an intervertebral disc, elbow, knee, shoulder, hip, temporo-mandibular joint, and so forth. In certain aspects of the invention, a living compartment comprises the cell-matrix construct of chondrocyte-like cells, such as are derived from HDFs, seeded in a biomaterial. The culture and differentiation of the living compartment may be initiated in vitro, in certain embodiments. The living core is seeded in the inert biomaterial and implanted, and the cells continue to proliferate and differentiate in vivo.

In certain embodiments, the cartilage that is the focus of application of the invention is intervertebral disc cartilage. In particular aspects of the invention, cells utilized in the invention are subjected to mechanical strain for chondrogenic differentiation. Thus, embodiments of the invention provide an inter-vertebral inert structure acting as an in vivo bioreactor for inducing growth and differentiation of a living core. In further embodiments, the invention provides a hybrid construct combining both an inert structure and living core for implantation into the inter-somatic space using a minimally invasive surgery.

It is an exemplary object of the present invention to provide a method intended to repair a degenerated intervertebral disc, e.g. restore intervertebral disc anatomy and improve its functioning. In particular aspects of the invention, there is provided a method to repair damaged disc using a hybrid structure made of an inert containing device intended to feed and differentiate an inner living core. Therefore, the inert structure acts as a delivery system of nutrients and growth factors and as a bioreactor able to differentiate autologous dermal fibroblasts into chondrocyte-like cells. Under mechanical stress (such as intermittent hydrostatic pressure, and/or fluid shear stress), the cells will acquire the characteristics of nucleus cells in the central part and annulus cells in the periphery. Exemplary fibroblast-derived chondrocyte-like cells may be harvested from skin, such as by a biopsy, and then seeded onto three-dimensional polymer scaffold for use of the repair of the disc. This would obviate the need for invasive technique to harvest autologous chondrocytes, in particular aspects. An advantage of certain aspects of the inventive hybrid construct that combines both an inert biomaterial acting as a nutrient-delivery system and living cells easily harvested from skin, for example, is that it is capable of self-maintenance or remodeling and may restore the disc function using a minimally invasive posterior surgical approach, for example.

In certain aspects of the invention, the damaged cartilage from the joint or intervertebral space is removed and the hybrid structure is installed within the space provided by the foregoing removal. In some embodiments of the invention, the device is implanted using a minimally invasive surgical procedure. In specific embodiments, an exemplary surgical technique is employed. In general embodiments for intervertebral discs, when an intervertebral disc must be removed from between two adjacent vertebrae, e.g. in the lumbar spine, it is less invasive to surgically proceed posteriorly from the back of the patient. This minimally invasive procedure allows proceeding with the curettage of the inter-somatic space through a small aperture within the annulus (annulotomy) for removing the degenerated fragments of the disc's nucleus. Using this small annulus opening, the present invention employs a novel intervertebral repairing pack that can be slid through the aforementioned incision and then expanded into the area generated by the nucleus removal within the inter-somatic space, for example. In specific embodiments, the removal of the damaged disc and the installation of the tissue-engineered construct are done in the same posterior operation, thereby minimizing risks, chances of surgical complications and re-interventions, as well as surgery time.

In one embodiment of the invention, there is an implantable device comprising a cells/scaffold composition and an encapsulating device, wherein the encapsulating device comprises a first generally concentric membrane; a second generally concentric membrane that is concentrically external to the first generally concentric membrane; a first volume within the first generally concentric membrane; a second volume that is external to the first generally concentric membrane and that is internal to the second generally concentric membrane; and a structure for extracting material from the second volume, wherein the first generally concentric membrane is semipermeable and houses the cell/scaffold composition. A membrane may be considered generally concentric compared to another if the centers of each of the membrane are substantially nearby.

In certain aspects of the invention, an individual is provided another therapy in addition to the implantable device of the invention. For example, before, during, and/or after implantation of the device, the individual may receive one or more antibiotics. Exemplary post-operative therapies includes Non Steroidal Anti-Inflammatory Drugs (NSAIDs), simple pain killers (analgesics), and/or myo-relaxing medication as needed, and it may be followed by a functional rehabilitation post-operatively, such as after the first, second, third or more post-operative week, for example.

In some embodiments, there is a hybrid structure for cartilage repair comprising an encapsulating device comprised of inert material and a living core comprised of chondrocyte-like cells. This encapsulating device acts as an in vivo bioreactor for cartilage engineering. It allows in vivo growth and differentiation of cartilage cells by providing growth factors and nutrients and transmitting a physiologic loading regimen.

In one embodiment of the invention, there is an implantable device, comprising a cells/scaffold composition; and an encapsulating device that comprises: a first membrane having an inside and an outside; a second membrane having an inside and an outside, wherein the first membrane is encapsulated inside the second membrane; a first volume disposed inside the first membrane; a second volume that is disposed outside the first membrane and that is disposed inside the second membrane; and a structure for adding fluid to the second volume, removing fluid from the second volume, or both, wherein the cells/scaffold composition is disposed inside the first membrane and the first membrane has one or more of the following characteristics: semi-permeable; biocompatible; biodegradable; and resorbable, wherein the second membrane has one or more of the following characteristics: biocompatible; hermetic to fluid; permeable to oxygen; resorbable; biodegradable; and expandable.

In a specific embodiment, the scaffold is comprised of a synthetic polymer, a natural hydrogel, or a synthetic hydrogel. In an additional specific embodiment, the synthetic polymer is polyglycolic acid, polylactic acid, polylactic-co-glycolic acid, poly-ε-caprolactone, or poly(glycerol-Sebacate) (PGS). In another specific embodiment, the synthetic polymer is a polyphosphazene, a polyanhydride, or a poly(orthoester). In particular embodiments, the natural hydrogel comprises collagen, hyaluronic acid, alginate, agarose, chitosan, fibrin, gelatin, or a copolymer thereof. In a further embodiment, the synthetic hydrogel comprises poly(ethylene oxide), poly(vinyl alcohol), poly(acrylic acid), poly(propylene fumarate-co-ethylene glycol), or a copolymer thereof.

In certain aspects of the invention, the cells in the device are chondrocyte cells or chondrocyte-like cells, such as wherein the chondrocyte cells or chondrocyte-like cells secrete a molecule selected from the group consisting of aggrecan, type II collagen, Sox-9 protein, cartilage link protein, and perlecan.

In particular cases, the cells were differentiated from fibroblast cells and/or stem cells. Exemplary fibroblast cells are dermal fibroblasts, tendon fibroblasts, ligament fibroblasts, synovial fibroblasts, foreskin fibroblasts, or a mixture thereof.

In particular aspects, the first membrane is comprised of a biodegradable, biocompatible, and resorbable polymer. In further aspects, the first membrane is comprised of a polyacrylate, a polyvinylidene, a polyvinyl chloride copolymer, a polyurethane, a polystyrene, a polyamide, a cellulose acetate, a cellulose nitrate, a polysulfone, a polyphosphazene, a polyacrylonitrile, a poly(acrylonitrile/covinyl chloride) or a derivative, copolymer or mixture thereof. In specific aspects, the first membrane is generated by polyelectrolyte complexation. In specific aspects, the second membrane is comprised of polyglycolic acid (PGA), polylactic acid (PLA), polylactic-co-glycolic acid (PLGA), poly-ε-caprolactone (PCL), polyurethane (PU), polydioxanone (PDO), a polyethylene, poly (glycerol sebacate) (PGS), or a derivative, copolymer, or mixture thereof. In additional embodiments, the rate of resorbability of the second membrane is slower than the rate of resorbability of the first membrane.

In particular embodiments, the implantable device comprises one or more nutrients, growth factors, and/or medicaments. In some cases, the implantable device may be further defined as comprising a basal cell culture medium comprising the one or more nutrients, growth factors, and/or medicaments. In specific embodiments, the medium is supplemented with Fetal Bovine Serum (FBS), ascorbic acid, and/or dexamethasone. The nutrients, growth factors, and/or medicaments may be present in the scaffold, the first volume, the second volume, or a combination thereof, in certain cases. The growth factor is selected from the group consisting of bone morphogenetic protein 2 (BMP-2), BMP-4, BMP-6, BMP-7, cartilage-derived morphogenetic protein (CDMP), transforming growth factor beta (TGF-β), insulin growth factor one (IGF-I), fibroblast growth factors (FGFs), basic fibroblast growth factor (bFGF), FGF-2, platelet-derived growth factor (PDGF), and a mixture thereof, in specific embodiments, and the medicament may be further defined as one or more of an antibiotic, antifungal agent, or antiviral agent.

In certain aspects of the invention, the structure comprises one or more tubes and/or comprises one or more catheters and/or one or more reservoirs. In particular cases, the structure is further defined as comprising one or more of a first tube; a second tube; optionally, a first reservoir; and optionally, a second reservoir. In a specific embodiment, the first and second tubes respectively comprise first ends positioned within the second volume, wherein the first and second tubes respectively comprise second ends connected to first and second reservoirs, or both. The first and/or second tubes are comprised of the same material as the second membrane, in one exemplary case, and the first and/or second tubes are comprised of silicone rubber, in one exemplary case.

In one embodiment of the invention, there is a method of repairing damaged cartilage in a joint (such as an intervertebral disc) of an individual, comprising delivering a device in accordance with the invention to the respective joint (such as intervertebral disc) of the individual. In a specific aspect, the method further comprises preparing the cells/scaffold composition under suitable ex vivo conditions. In another specific embodiment, preparing the cells/scaffold composition is defined as subjecting one or more cells to a scaffold under suitable conditions. Preparing of the cells/scaffold composition may occur for no less than about two to three days, in certain aspects of the invention. In a specific embodiment, the suitable conditions allow proliferation of the cells, such as, for example, allowing the stimulation of chondrogenic differentiation. Suitable conditions may be further defined as being under high density micromass culture, being under low oxygen tension (between about 1.0%-7.5%), being under mechanical stress, and/or being fed by a medium supplemented with growth factors, ascorbic acid, and/or dexamethasone, in exemplary embodiments.

In particular embodiments, the cells/scaffold composition is subjected to mechanical stress, which may be hydrostatic pressure, fluid shear stress, or a combination thereof, for example. In a specific embodiment, the mechanical stress is intermittent. In particular cases, the mechanical stress is fluid shear stress and the scaffold is microfluidic scaffold.

In other particular embodiments, the delivering step is defined as implanting the device using minimally invasive surgery. In one exemplary case, following implantation of the device into the individual, the second membrane is inflated to fill a void in the joint, such as an intervertebral disc. In another exemplary case, prior to delivery of the device to an intervertebral disc of the individual, at least part of an endogenous intervertebral disc was removed from the individual. The joint of concern with the invention may be an intervertebral disc, a knee, a shoulder, an elbow, a hip, or a temporo-mandibular joint, in specific embodiments.

In certain aspects of the invention, the structure of the device comprises: a first tube having first and second ends, said first end of the first tube disposed within the second volume; a second tube having first and second ends, said first end of the second tube disposed within the second volume; a first reservoir; and a second reservoir, wherein following delivery of the device to an intervertebral disc in the individual and following inflation of the second membrane, the second ends of the first and second tubes are respectively connected to the first and second reservoirs. In a specific embodiment, the first and second reservoirs are subcutaneously positioned in the individual. Methods of the invention may further comprise sealing the first membrane, sealing the second membrane, or both. In a specific aspect, at least part of the second volume is exchanged. In one exemplary embodiment, the method of the invention further comprises removing at least part of the second volume through the first reservoir. In another specific aspect, the method comprising removing fluid from the first or second reservoir, delivering a fluid to the respective second or first reservoir, or concomitantly removing fluid from the first or second reservoir and delivering a fluid to the respective second or first reservoir.

In certain cases, the cells/scaffold composition is inserted into the first membrane prior to delivery of the device into the individual or wherein the cells/scaffold composition is inserted into the first membrane subsequent to delivery of the device into the individual. In a specific embodiment, the first membrane is inserted into the second membrane prior to delivery of the device into the individual or wherein the first membrane is inserted into the second membrane subsequent to delivery of the device into the individual.

In one embodiment of the invention, there is a method of preparing a cells/scaffold composition, wherein the cells are chondrocytes or chondrocyte-like cells, comprising: subjecting cells capable of differentiating into a chondrocyte-like cell to the scaffold; subjecting the cells to mechanical stress; and optionally subjecting the cells to one or more growth factors suitable for differentiation to a chondrocyte or chondrocyte-like cell. In a specific embodiment, the mechanical stress is intermittent.

In a further embodiment, there is a kit comprising the device of the invention, wherein the device is housed in one or more suitable containers. In specific embodiments, the kit further comprises cells that are chondrocyte cells, chondrocyte-like cells, or cells that are capable of differentiating to chondrocyte cells or chondrocyte-like cells.

In an additional embodiment, there is an implantable device, comprising: a cells/scaffold composition encapsulated inside a membrane, said membrane having an inside and an outside; and a structure for exchanging at least part of fluid that is inside the membrane, wherein the membrane has one or more of the following characteristics: semi-permeable; biocompatible; biodegradable; and resorbable.

In another embodiment, there is a hybrid structure for cartilage repair, comprising: an encapsulating device comprising inert material; and a living core comprising chondrocyte-like cells, wherein said encapsulating device encapsulates the living core.

In an additional embodiment, there is an in vivo bioreactor for cartilage engineering, comprising a device that encapsulates cells, wherein said cells are capable of differentiating to chondrocytes or chondrocyte-like cells, wherein the encapsulation of said cells provides suitable conditions for in vivo growth and differentiation of said cells, wherein said conditions comprise providing a physiologic loading regimen on said cells. In a specific embodiment, the physiologic loading regimen comprises force from a spine of an individual.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention. The present application refers to a number of references and documents all of which are incorporated herein in their entirety.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

Figure 1:
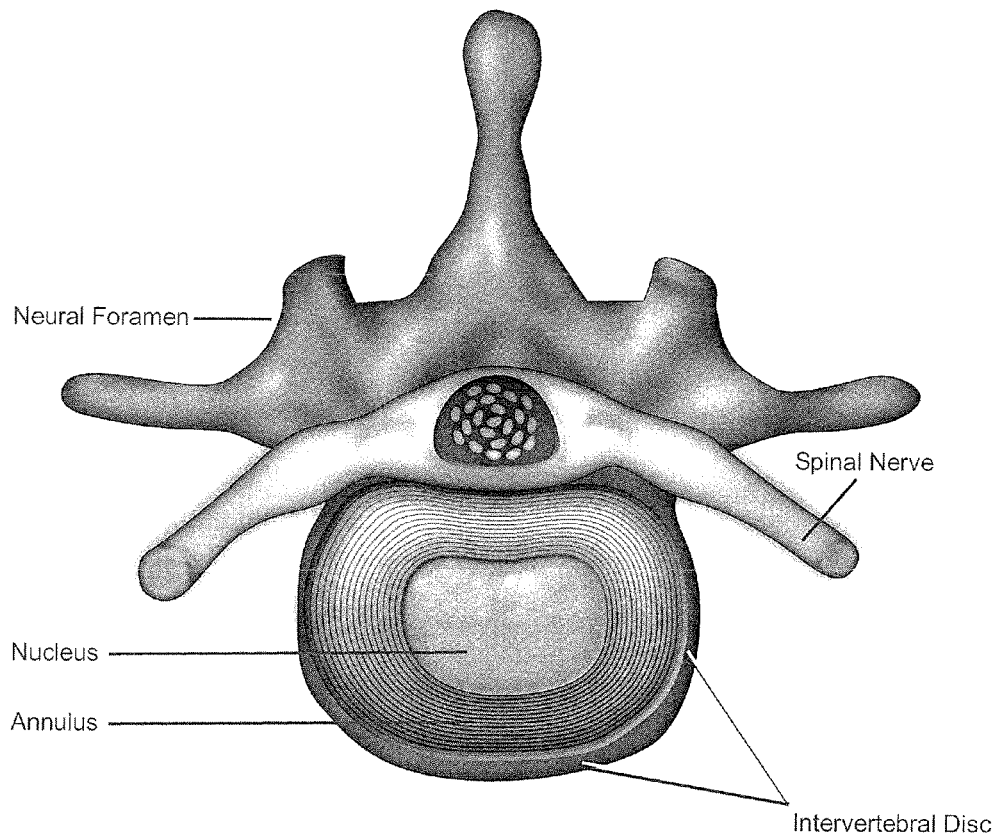
FIG. 1 illustrates a cross-section of the exemplary L4-L5 intervertebral space.
Figure 2:
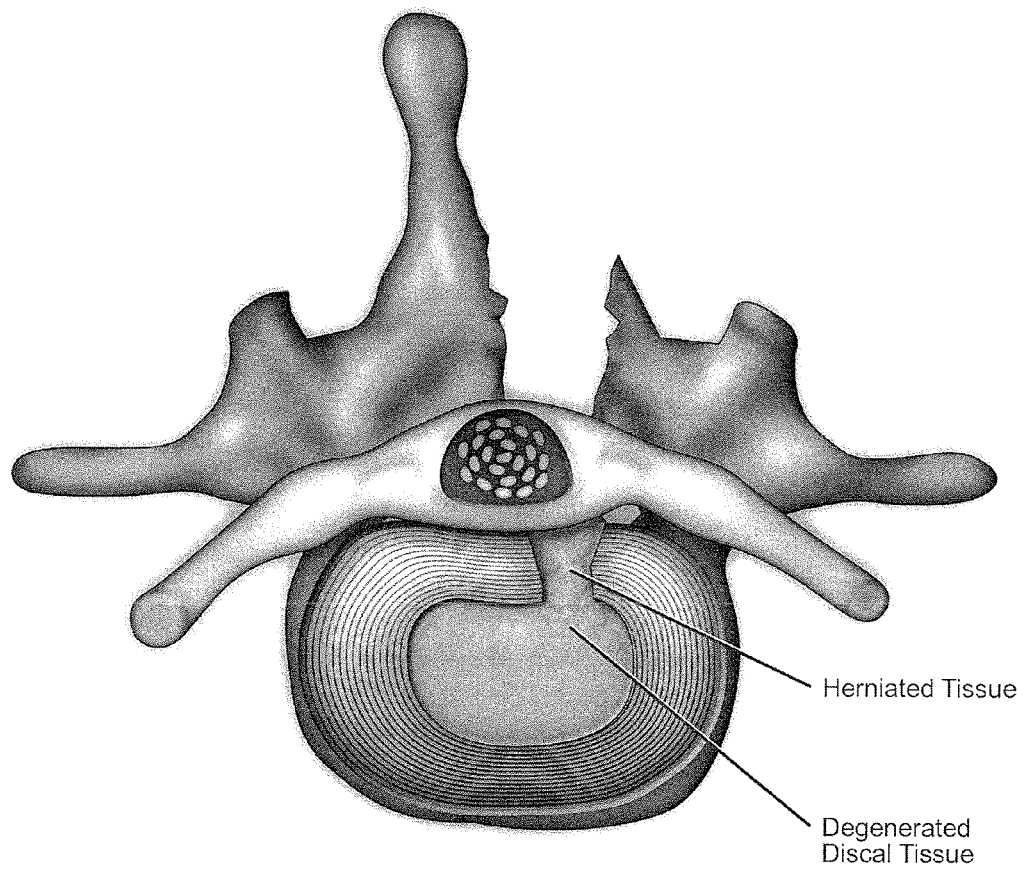
FIG. 2 shows a posterior approach to an intervertebral space, including exemplary herniated tissue and degenerated discal tissue.
Figure 3:
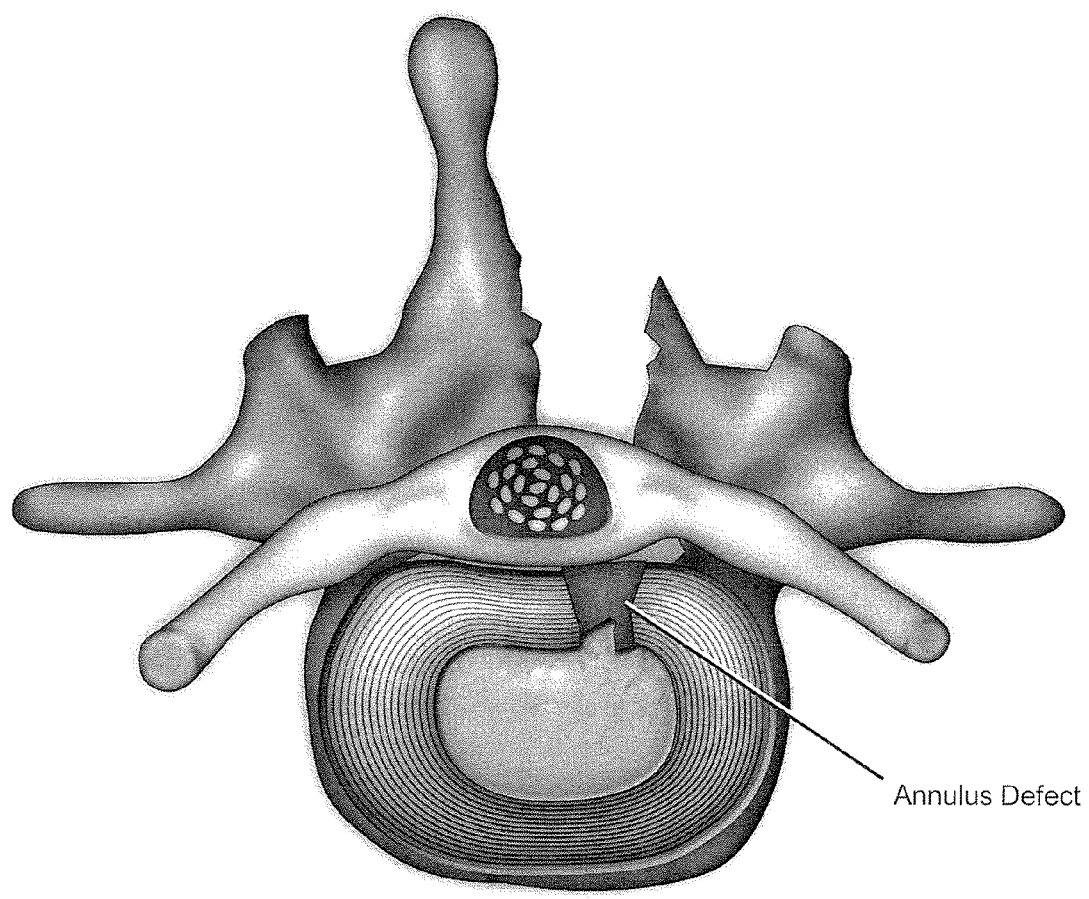
FIG. 3 illustrates an exemplary embodiment of the annulus defect location for disc removal.
Figure 4:
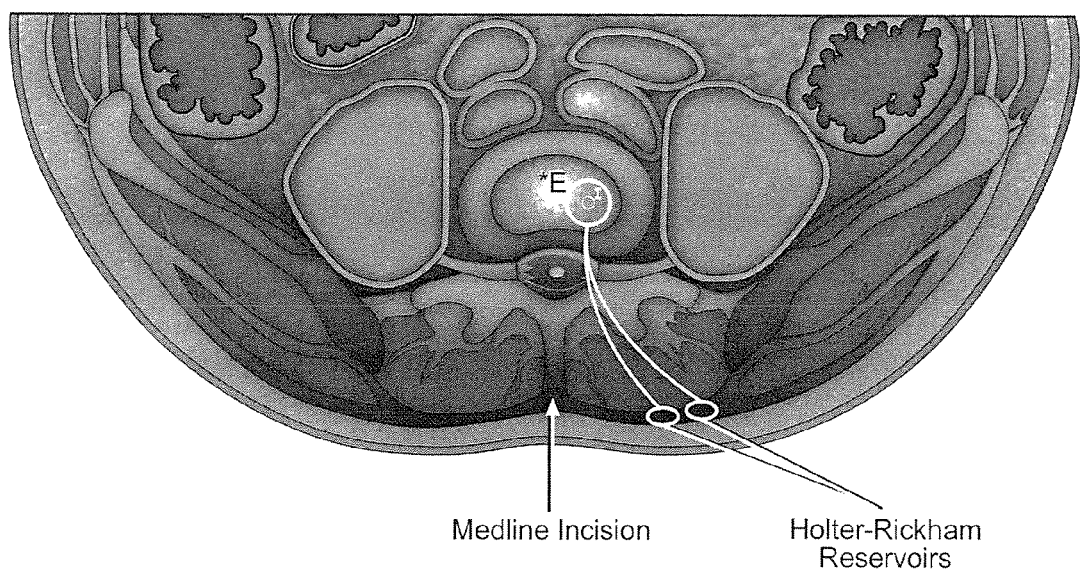
FIG. 4 shows abdominal cross-section and draining system in embodiments of the invention, including an exemplary medline incision and exemplary Holter-Rickham reservoirs (Codman & Shurtleff, Inc.; Raynham, Mass.)

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein.

I. Definitions

The term "bioreactor" as used herein refers to a system in which a biological conversion is effected. Cells are cultivated in a controlled manner and are converted via specific reactions, in specific embodiments. In some aspects of the invention, a bioreactor is capable of regulating one or more of the following parameters: temperature, medium pH, exchanges of gases, mechanical stimuli, $pO_2$, $PCO_2$, and humidity. A perfusion system is present in the bioreactor (perfusion-bioreactor), in specific embodiments, to provide constant supply of nutrients and to remove efficiently the waste products. Mechanical stresses are an important factor of chondrocyte function. Combinations of mechanical stresses are simultaneously developed during joint motion on an intermittent basis that includes cell and tissue deformation, compressive and shear forces, fluid flow, and changes in hydrostatic pressure, for example. These conditions are reproduced with the bioreactor, in certain aspects.

The term "catheter" as used herein refers to a hollow tube, which may be flexible or rigid, that is employed to drain fluid from an area in the body.

The term "chondrocyte-like cells" as used herein refers to cells that are not primary chondrocytes but are derived from stem cells (such as mesenchymal stem cells) or cells from other lineages (such as fibroblasts). These chondrocyte-like cells have a phenotype of chondrocytes (cells of cartilage). This means that not only do they have a shape of chondrocytes (polygonal and/or rhomboidal cells, for example), but also they are able to aggregate and produce cartilage matrix components, such as sulfated proteoglycan and type II collagen, for example. Thus, exemplary markers of chondrocyte-like cells include one or more of aggrecan, which is a chondroitin sulfate and keratan sulfate proteoglycan, type II collagen, Sox-9 protein, cartilage link protein, and perlecan, which is a heparan sulfate proteoglycan, for example.

The term "copolymer" as used herein refers to a polymer comprising two or more different monomers (polymer: a naturally occurring or synthetic compound comprising large molecules made up of a linked series of repeated simple monomers).

The term "de-differentiation" as used herein refers to regression of a specialized cell or tissue to a simpler, more embryonic, unspecialized form. When chondrocytes are grown ex viva in monolayers, they lack their in vivo environment (and especially the three dimensionality and mechanical stress) and undergo morphological and molecular changes called de-differentiation. This process involves a change in morphology and a change from expression of chondrocyte-specific genes to that of genes that are normally expressed in fibroblasts.

The term "discectomy" as used herein refers to a procedure to remove part or all of a degenerated nucleus through a fenestration within the annulus. It is performed through a minimally invasive approach using an operative microscope. The procedure frees the roots by removing the compressive herniated (extruded) nucleus. It allows removing the degenerated remaining nucleus through a tenotomy (aperture) within the annulus. In particular, a discectomy is actually a herniectomy with the removal of the degenerated nucleus fragments.

The term "encapsulate" or "encapsulating" as used herein refers to enclosing within a boundary, such as in a membranous sac.

The term "fluid shear stress" refers to the motion of fluids upon a surface, which results in the generation of shear stress. Shear stress is a stress state where the stress is parallel to a surface. Microfluidic scaffold allows fluid flow in the microchannels. This fluid flow induces fluid shear stress on the cells seeding in the scaffold.

The term "hermetic" as used herein refers to being made liquid-tight, such as by fusion or sealing, for example. In particular, a hermetic membrane does not allow liquid inside it to exit the membrane, although it allows oxygen and carbon dioxide to cross the membrane (such as oxygen to enter the membrane and carbon dioxide to leave the membrane).

The term "hydrostatic pressure" refers to the pressure exerted or transmitted by liquid (for example, water) at rest. The intervertebral disc is exposed to wide ranges of intradiscal hydrostatic pressure during different loading exercises and are at their minimum (about 0.25 MPa) during lying or relaxed sitting and at maximum (about 2.5 to 5 MPa) during lifting weights with a round back. These different loading magnitudes influence the intervertebral disc by alteration of disc matrix turnover depending on their magnitudes. Numerous studies have been done to determine the best regimen for intermittent hydrostatic pressure (IHP) to be applied in vitro to the cells to induce chondrogenic differentiation of cells in vitro. Different regimens have been tested. In these studies, IHP applied is within the amplitude ranges from 0.5 MPa to about 5 MPa and a frequency range from 0.01 Hz to 1 Hz. The encapsulating device is designed to transmit in vivo hydrostatic pressure to the cell-matrix construct, in specific embodiments. The external envelop filled with liquid (medium) is compressed during different loading exercises; under this compression some liquid medium diffuses through the semi-permeable internal membrane, which allows perfusion of the cell-matrix construct and generates hydrostatic pressure within the cell-matrix construct. In this system, the appropriate physiologic hydrostatic pressure is applied to the cell-matrix construct, which is useful for chondrogenic differentiation of the cells.

The term "hypoxia" as used herein refers to a deficiency in oxygen. In specific aspects, it refers to oxygen tension that is less than about 20%.

The term "joint" as used herein refers to a region in the body wherein two bones of a skeleton join.

The term "membrane" as used herein refers to a pliable layer of material that separates different types and/or areas of biological material. It may be comprised of natural and/or synthetic material, and it may be permeable to substances in solution, for example.

The term "microfluidic scaffold" as used herein refers to a material that comprises a system of microchannels.

The term "minimally invasive surgery" as used herein refers to procedures performed through one or more small incisions in an individual. For example, in certain aspects minimally invasive surgery uses specialized techniques, miniature cameras with microscopes, tiny fiber-optic flashlights and/or high definition monitors. For the individual, minimally invasive surgery means less trauma to the body, less blood loss, smaller surgical scar(s) and less need for pain medication, when compared to conventional open surgery. Individuals are suited to leave a medical facility sooner after minimally invasive surgery and return to normal activities sooner than with conventional open surgery.

The term "reservoir" as used herein refers to a device that acts as an injection chamber. In specific embodiments, the type of reservoir may be one that is routinely used in the art to deliver drugs (antibiotics for example, in case of meningitis or ventriculitis), into the cerebral ventricular system (hence the term of "ventriculostomy"), into a vein (chemotherapy for oncologic purpose), or into the subarachnoid spinal space (morphine for pain relief), for example. It may be considered to be a kind of drug delivery system, in particular aspects. It is comprised of several parts: 1) a silicone-based (called "silastic") material top that allows repeated punctures without losing its waterproof characteristics; 2) a stainless-steel base that avoids the needle to injure the underlying tissues; and 3) a silastic end that connects to a catheter. The catheter may also be made of silastic. Its distal end can be brought to the site and cut at the right size, while its proximal end is connected to the reservoir's end. The exemplary system defines a 1 to 2 $cm^3$ chamber, hence its name of "reservoir" (tank).

The term "scaffold" as used herein refers to a porous biodegradable polymer construct that supports cell growth and/or migration, for example.

The term "seeding" as used herein refers to implanting cells in a scaffold. The cells will attach to the scaffold and then grow and differentiate in the scaffold.

II. General Embodiments of the Invention

In general embodiments of the invention, there is provided a device and methods of its use, wherein the device comprises cell-matrix construct of chondrocyte-like cells encapsulated in a multilayered membrane. Although any tissues may be repaired at least in part by methods of the invention, including any cartilage tissues, in a particular exemplary embodiment, intervertebral disc cartilage or joint cartilage is repaired. Exemplary methods of the invention utilize a combination of a living core and inert core or structure, thereby providing a hybrid structure. In particular aspects of the invention, the living core comprises a cell-matrix construct of chondrocyte-like cells, such as are derived from HDFs, and the inert structure comprises the living core and is implanted into a patient using a minimally invasive surgical procedure, for example.

The present invention provides a method for biological repair of cartilage using autologous Human Dermal Fibroblasts (HDFs) as cell sourcing. The present invention also provides a device comprising a cell-matrix construct of cells, such as chondrocyte-like cells, that are encapsulated in a multilayered membrane. In a particular embodiment, the invention concerns growth and differentiation of cells in vivo using a special device. The chondrogenic differentiation is induced by mechanical stress, and in particular aspects, Intermittent Hydrostatic Pressure (IHP) and/or fluid shear stress, for example.

A general embodiment of the invention is to use HDFs as cell sourcing for engineering new cartilage for the intervertebral disc, because these cells are easy to harvest and to grow. The idea is to induce differentiation of these cells into chondrocyte-like cells. There is already some evidence for chondrogenic differentiation of HDFs into chondrocyte-like cells. However, these studies are only in vitro and the technique to differentiate the cells is based on the use of specific growth factors, hypoxia, or specific matrix such as aggrecan.

Because of its design, this device allows one or both of the following, for example: 1) diffusion of nutrients and oxygen to the living cells; and/or 2) transfer of the load onto the cells. This mechanical force and especially the IHP is critical for chondrogenic differentiation of fibroblasts. It is known that IHP is the most potent stimulus for induction and maintenance of the chondrocyte phenotype. When chondrocytes are harvested from cartilage to be used to engineer in vitro new cartilage, these cells need to be expanded but this causes the chondrocytes to dedifferentiate. It has been shown that IHP can redifferentiate the cells into chondrocytes. People who are using chondrocytes to engineer cartilage in vitro often use mechanical strains and especially IHP as inducer of differentiation. However, there is nothing in the literature on the effects of IHP on chondrogenic differentiation of HDFs.

In embodiments of the invention, there are at least two components to the device: 1) cell-matrix construct, wherein the cells (HDFs, for example) are seeded into a scaffold (and cells that do not attach to the scaffold may be washed away); 2) encapsulating device. In specific embodiments, the in vivo encapsulating device is comprised of two concentric membranes, in specific embodiments: 1) an internal membrane is a semipermeable membrane that wraps the cell-scaffold construct (this semipermeable membrane is permeable to small molecules and so allows diffusion of nutrients and oxygen and elimination of wastes, but it is impermeable to macromolecules such as collagen and glycosaminoglycans, for example; these macromolecules that from the natural extracellular matrix are then retained within the scaffold); and 2) an external membrane is hermetic to fluid but permeable to oxygen, and it is expandable and inflatable in order to be implanted through a minimally invasive posterior surgical procedure (in specific embodiments, when expanded it will fit the cavity of discectomy, for example exactly fit the cavity). The external membrane is filled with medium which nourish the cells. The fluid enclosed within the envelop forms a fluid environment that transfers IHP to the living cells. About the day after surgery, when the individual can stand up and begin to walk again, he applies some load on the spine and especially on the instrumented level. Therefore, the living core receives the right cyclic hydrostatic pressure regimen under physiological load through the envelop that is filled with medium, which is useful for HDFs growth and conversion. Thus, in certain aspects the individual walks within about one day of implantation of the device, about two days, about three days, about four days, or about five or more days following implantation of the device.

In specific embodiments, the external membrane filled with medium is connected to a draining system to regularly change the medium. The chondrogenic differentiation of HDFs is induced by mechanical stress and especially Intermittent Hydrostatic Pressure (IHP) and/or fluid shear stress in vitro and then in vivo. Exemplary co-culture conditions are as follows: high density micromass culture, supplementation with BMP-2, ascorbic acid, and hypoxia, for example.

This invention solves many of the problems in the field. The nutrients and growth factors are provided to the cell-matrix construct by the in situ medium. It avoids the problem of diffusion of nutrients from the surrounding natural tissue (endplates) which is usually deficient due to degeneration of these structures. Growths factors important for chondrogenic differentiation of HDFs are added to the medium. In specific aspects, HDFs are employed, which avoid the use of invasive technique to harvest chondrocytes. HDFs, or any other cells, are pre-differentiated in vitro for a short period of time and continue to grow and differentiate in vivo. The encapsulating device with its external envelop filled with fluid will provide the physiologic loading and compressive forces ideal for chondrogenic differentiation of HDFs.

III. The Hybrid Construct

The invention employs a hybrid construct for repair of cartilage in a joint, such as an intervertebral disc. Exemplary embodiments of the hybrid construct are described herein, and in certain aspects the hybrid construct is an implantable device, for implantation into a mammal, such as a human, dog, cat, horse, pig, sheep, goat, and so forth. In particular aspects, a hybrid construct is comprised of at least a living core, comprising cells and a scaffold, and an inert structure.

A. Cells/Scaffold Composition

The living core, which may be referred to as the cells/scaffold composition, is a cell-matrix construct and comprises cells seeded in a scaffold (which may be referred to as a matrix). In a specific embodiment, the scaffold comprises alginate beads; a microfluidic scaffold (the Microfluidic scaffold could be made of any biodegradable biopolymer [organic biodegradable polymers: poly(L-lactic acid) (PLA), poly(glycolic acid) (PGA), poly-lactic-co-glycolic acid (PLGA) natural hydrogels (collagen, HA, alginate, agarose, chitosan, combination collagen/HA, chitosan/GAG, collagen GAG); and/or synthetic hydrogels (Poly(ethylene oxide), (PEO), poly(vinyl alcohol) (PVA), poly(acrylic acid) (PAA), poly (propylene fumarate-co-ethylene glycol) (P(PF-co-EG))], for example. In specific embodiments, cell adhesion ligands such as peptides or polysaccharides are employed. The peptide sequences may be capable of binding to cellular receptors. These peptides could comprise the exemplary amino acid sequences arginine-glycine-aspartic acid (RGD), argininine-glutamic acid-aspartic acid-valine (REDV), tyrosine-isoleucine-glycine-serine-arginine (YIGSR), or isoleucine-lysine-valine-alanine-valine (IKVAV) and may be attached to the scaffold, wherein the ligands and/or growth factors may be incorporated to regulate cell fate. In fact, the growth factors can be incorporated in the scaffold or included in the medium in the external membrane, for example. The scaffold materials may be biodegradable, and the rate of biodegradation can be manipulated.

In accordance with the invention and as explained above, HDFs are differentiated into chondrocyte-like cells under mechanical stress either in vitro or in vivo or both in vitro followed by in vivo, for example. As explained above, important co-culture conditions include high cell density culture; growth factors (BMP-2); and/or ascorbic acid, for example. HDFs can also be differentiated into chondrocyte-like cells under low oxygen tension and culture on aggrecan with insulin growth factor one (IGF-I). As aforementioned, bioreactors are used to induce in vitro proliferation and differentiation of HDFs. The inert structure of the present invention is used to induce in vivo differentiation, in particular aspects of the invention. HDFs in alginate beads or HDFs seeded in a microfluidic scaffold or HDFs seeded in any other polymeric scaffold are encapsulated in a semi-permeable membrane that is part of an inert structure, in specific embodiments of the invention. A function of the semi-permeable membrane is to encapsulate the chondrocyte-matrix construct to concentrate the production of ECM proteins. This membrane allows the passage of $O_2$, nutrients/waste, and $CO_2$, for example.

In specific embodiments, scaffold refers to a porous biodegradable polymer construct to support cell growth and/or migration. This material is non-toxic, biocompatible and biodegradable, in specific embodiments.

In exemplary embodiments, alginate is employed for the scaffold. Alginate is a natural polysaccharide isolated from seaweed. It is a polysaccharide composed D-mannuronate and L-guluronate monomers. When crosslinked with calcium ions, it forms a gel that is biocompatible, biodegradable. Alginate is well established as matrix material for tissue within regenerative medicine. It has been used more widely than other hydrogels to assess in vivo potential of hydrogel scaffolds for cartilage engineering. Macrobeads of alginate (1-3 mm in size) or microbeads of alginate (250-500 µm) can be used in this invention. Microbeads of alginate are preferred. These smaller beads have the advantage of a higher surface to volume ratio allowing good transport of essential nutrients, they are also less fragile. Alginate is biocompatible and approved by the U.S. Food and Drug Administration for human use.

HDFs may be seeded in alginate macrobeads (as described below) or preferentially in alginate microbeads. There are different techniques known in the art to generate alginate microbeads. There are usually produced by electrostatic droplet generation. For example, HDFs can be seeded in alginate microbeads as follows. Alginate powder (Sigma, St Louis, Mo.) is dissolved in WFI water at a concentration of 2.2% w/w and then mix with a suspension of HDFs in culture medium to obtain final concentrations of 1.5% w/w alginate and $10^7$ cell/ml. Alginate microbeads are then produced by electrostatic droplet generation. In brief, cell/alginate suspension is extruded through a positively charged blunt stainless steel needle at a constant flow rate of 14.0 ml/h by a syringe pump and resulting droplets are collected in a gelling bath (1.5 w/v $CaCl_2$). As $Na^+$ ions are exchanged with $Ca^{2+}$ ions, alginate droplets harden and form insoluble microbeads with entrapped cells. The microbeads are left for 30 min in the gelling bath in order to complete gellation.

Microfluidic scaffolds may also be employed, in particular embodiments. They are complex scaffolds with micron-scale resolution. These scaffolds present a network of micro-channels that allow fluid flow within the scaffold. This network of micro-channels helps to provide both nutrients and soluble factors to distinct sections of the scaffold. These scaffolds can be made of different biopolymers. They can be made of synthetic polymers such as polyglycolic acid (PGA), polylactic acid (PLA), polylactic-co-glycolic acid (PLGA); synthetic hydrogels such as poly(ethyleneoxide) (PEO), poly (vinyl alcohol) (PVA), poly(acrylic acid) (PAA), poly (propylene fumarate-co-ethylene glycol (P(PF-co-EG), or of Poly(glycerol-Sebacate) (PGS) that is a biodegradable elastomer. In the invention, this microfluidic scaffold is encapsulated with a semi-permeable membrane. This semi-permeable membrane allows the perfusion of medium containing nutrients and growth factors within the scaffold. By circulating within the network of micro-channels, the medium will apply fluid shear stress on the cells seeded in this scaffold. This mechanical force is critical for chondrogenic differentiation of HDFs.

B. The Inert Structure

In the invention, the hybrid construct employs an inert structure as part of its composition. Functions of the inert structure may be biological (delivery of nutrients and/or growth factors) and or mechanical (to transfer mechanical forces, such as onto the cells/scaffold composition; such forces may include IHP and/or Fluid shear stress), for example. The inert structure may function as an "in vivo bioreactor" by transferring mechanical strain and by providing medium (by perfusion through the semi-permeable membrane) to the cells/scaffold composition.

In certain embodiments, functions of the inert structure include one or more of the following: 1) to hermetically encase the living core; 2) to act as a semi-permeable membrane by allowing certain molecules (for example nutrients, growth factor, etc.) to pass through it by diffusion (and occasionally specialized "facilitated diffusion") under certain physico-chemical conditions (for example, hydrostatic pressure, osmotic concentration, temperature, etc.); 3) to transfer the load and to share the dynamic mechanical stress (hydrostatic pressure) to the living compartment acting as an inducer of cell differentiation; and/or 4) to act as an in vivo bioreactor.

The inert structure may be considered an encapsulating device, in specific embodiments. For certain embodiments, it is designed to apply mechanical stress on the cells seeded in the three-dimensional scaffold composition. The external membrane of the encapsulating device is filled with fluid (medium). The fluid enclosed within the envelop forms a fluid environment that transfers the cyclic hydrostatic pressure to the living cells. When the patient stands up, for example, he applies some load on his spine that is transferred to the living cells through the external envelop that is filled with fluid. This membrane provides the physiologic loading and compressive forces suitable for chondrogenic differentiation of cells such as HDFs. In the case of cells embedded in a microfluidic scaffold, the medium circulating within the micro-channels also apply fluid shear stress on the cells. This fluid shear stress is another force that induces chondrogenic differentiation of cells.

In specific embodiments, the membrane is generally balloon-shaped, and in additional embodiments the membranes are generally concentrical with one another. In further specific embodiments, the inert structure comprises two expandable balloon-like bio-polymers, namely, internal balloon "I," which is enclosed within an external balloon "E". Hence, the inert structure comprises two concentric envelopes capable of being successively inflated and having inflation activity. In certain aspects, a number X of membranes may be utilized in the device, wherein X is any whole integer greater than one. That is, X balloons may be installed concentrically as with layers in an onion, each of them defining a space with a specific function (for example, for waste, media, oxygen, and/or for connecting the graft to natural tissue).

In one embodiment, the external balloon, layer or envelope "E" comprises a biocompatible resilient, inflatable, hermetic, expandable, and/or resorbable (time $T_1$, wherein $T_1$ is the time for complete resorption of "E") material that is able to be sealed once installed in the cavity. In specific embodiments, external balloon "E" is capable of having or has one or more of the following activities: 1) to receive a second internal balloon or layer or envelope "I" enclosing the cells (in the form of cell-matrix construct, or cell solution or graft); 2) to be inflated with a media (for example, liquid) or to expand its wall (for example, via swelling) in order to fill the cavity resulting of the discectomy; and 3) to close the annulus defect to prevent it from "herniating" or coming out from the inter-somatic space through the tenotomy incision once the construct is under load.

In one embodiment, the internal balloon or layer "I" comprises a biocompatible, resilient, inflatable, semi-permeable, and/or resorbable (time $T_2<T_1$, wherein $T_2$ is the time for complete resorption of "I") material that is able to seal the living core once installed into the external layer. The internal balloon (envelop, membrane, or layer) "I" is capable of having or has the following activities: 1) to hermetically wrap up the living core; 2) to act as a semi-permeable membrane by allowing certain molecules (for example, nutrients, growth factors, etc.) to pass through it by diffusion (and occasionally specialized "facilitated diffusion") under certain physico-chemical conditions (for example hydrostatic pressure, osmotic concentration, temperature, etc.); and 3) to transfer the load to the living core so as to share the dynamic mechanical strain therewith, thereby acting as an inducer of cell differentiation.

In accordance with an aspect of the invention, the combination of an external compartment media (such as a liquid, for example) or swelled wall (such as hydrated hydrogel, for instance) "E" and the internal semi-permeable envelope provide a delivery system of nutrients and growth factors capable of feeding an inner living core. These envelopes also transfer the mechanical forces, including hydrostatic pressure to the living core.

The inert structure is an encapsulating device intended to wrap up, feed and differentiate a living core made of cells, such as HDFs.

In a preferred embodiment, the inert structure comprises two expandable balloon-like bio-polymeric membranes, namely, internal membrane "I" which enclosed within an external membrane "E". Hence, the inert structure comprises two concentric envelops intended to be successively inflated. At the rest position, the two envelopes "I" and "E" are flat, deformable, shaped and fit one another. Both can be sealed once implanted. The inert structure composition may be determined by the choice of tissue engineering system, in specific embodiments.

The external envelope "E" comprises a material that is inflatable (in order to be implanted flat through a minimally invasive posterior approach, then loaded with the living core, and then inflated with the media solution); resilient (to transfer load sharing onto the living core); expandable (to allow its expansion and fill the cavity resulting of the discectomy); permeable to $O_2$ but hermetic to fluids: relative hypoxia is a useful parameter of HDFs conversion, but $O_2$ tension within the natural disc is appropriately low; biodegradable (to allow the graft to reconnect with the natural remaining disc); biocompatible (to minimize inflammatory reaction); resorbable (time T1); or a combination thereof.

"E" may be positioned in a joint, for instance, into the cavity resulting of the curettage of an inter-somatic space between a pair of adjacent vertebrae and within the remaining discal tissue, in specific embodiments. It also may be mechanically able to maintain the disc height under loading. In additional embodiments, "E" receives a second internal balloon "I" enclosing the living core. "E" may be inflated with a fluidic solution (for instance the media) to extend in the chamber (cavity resulting of the discectomy) peripherally up to the remaining discal tissue and fill the cavity. "E" is configured such that it allows changing of the media (removal of metabolic wastes and/or replenishment of nutrients and/or growth factors, for example), such as under an isobaric regimen, for example. "E" acts as an in vivo bioreactor by transferring the load sharing onto the living core, for example with cyclic hydrostatic pressure (which is useful for differentiating cells into chondrocyte-like cells), in certain aspects. In particular embodiments, the configuration of "E" produces relative hypoxia due to its characteristics (Hypoxia or hypoxia-mimicking agent, as lactate, induces HDFs conversion in chondrocytes-like cells). "E" may also close the annulus defect (tenotomy opening) to prevent it from "herniating" or coming out from the inter-somatic space through the tenotomy incision once the construct is under load.

In certain aspects of the invention, the internal membrane "I" comprises a membrane that is biocompatible; resilient; inflatable (while the media is consumed, the living core grows and expands to the inner wall of the external membrane); semi-permeable (controlled release system for nutrients, growth factors, etc.); biodegradable (so as not to interfere with the long-term properties of the repaired tissue); and resorbable (time $T_2 < T_1$). E" must resorb after "I" not only to avoid the leakage and the lost of the media while the living core is not mature yet, but also to keep the fragile "I" away from any direct mechanical strain). In other certain aspects, "I" hermetically wraps up the living core; acts as a delivery system of nutrients and growth factors capable of feeding an inner living core through a semi-permeable membrane by allowing certain molecules (for example nutrients, growth factor etc.) to pass through it by diffusion (and occasionally specialized "facilitated diffusion") under certain physic-chemical conditions (for example hydrostatic pressure, osmotic concentration, temperature, etc.)

These two membranes ("E" and "I") define 2 volumes $V_E$ and $V_I$. These two distinct volumes may have different shapes (spherical, cylindrical, conical, etc.) depending of the contour of the inter-vertebral cavity and the load sharing. In specific embodiments, the device conforms to the shape of the cavity.

Volume $V_E$ is defined as the space that separates membrane "E" from membrane "I". It comprises nutrients and growth factors (media) to be delivered to the cells, in specific embodiments, such as through the semi-permeable membrane "I". It also acts as a load-bearing structure capable of transferring mechanical strain, for example the cyclic hydrostatic pressure regimen or the high fluid shear stress (due to its high content water) to the living core (which induces chondrogenic differentiation of cells, such as HDFs).

Volume $V_I$ is defined as the space that is outwardly limited by the internal semi-permeable membrane "I" and comprises the living core made of chondrocyte-like cells, such as cells derived from HDFs.

Until the living core has become viable (e.g. capable of self maintenance) the media enclosed in $V_E$ may be regularly changed in order to remove any toxic wastes accumulated due to the metabolism (free radicals and/or lactic acid, for example), as well as any other cellular scraps or debris as a result of the cellular growth. Such a change allows replenishment of its contents with nutrients and/or growth factors. In specific embodiments, this procedure is performed periodically, such as one or more times per week or month, for example at least once a week, such as twice a week. In additional specific embodiments, it requires to equip "E" with an additional feature for draining $V_E$. This draining system may be made of one or more tubes and one or more reservoirs, in certain aspects, and in particular embodiments it comprises two tubes and two reservoirs. The first tube may be employed to remove the used media, and the second tube may be employed to inject the new media. Each of these tubes (or catheters) comprises a proximal end that hermetically connects to $V_E$ and a distal end that connects to a reservoir. These catheters could be made either of the same material as "E" or of silicone rubber, for example. Their length may be of any suitable length so long as they can span from the reservoir to the device. They may be comprised between about 10 and 15 centimeters, and is pre-operatively set up by cutting their distal end at the appropriate length according to the depth of the operative site and the anatomical data (patient's morphology). Their outer diameter may be of any suitable length, but in specific embodiments they are about 2.5 millimeters in length, such as in order to be small enough to exit from the tenotomy aperture, not to compress or injure the adjacent root, and allow a 1.2 millimeter inner diameter.

The tubes may be implanted at the end of a discectomy procedure, after implantation, inflation and sealing of the bio-reactor, and before skin closure. They may be connected to the distal end of each tube (catheter). Then, each reservoir may be subcutaneously positioned so that it can be reachable by a needle from the skin (percutaneous puncture).

In one embodiment, the engineered living core is pre-encapsulated with "I" and then slid into "E". While the media is consumed, the living core expands to the inner wall of the envelope "E". The envelop "E" resorbs and the graft reconnects with the natural remaining disc.

1. The Internal Semi-Permeable Membrane

The internal envelop comprises the living core, includes a controlled release system (in order to allow the feeding of the living core with the media through its semi-permeability characteristics), is expandable (while the media is consumed, the living core expands to the inner wall of the external membrane), and/or is biodegradable (so as not to interfere with the long-term properties of the repaired tissue), for example.

In specific embodiments, the internal membrane is a semi-permeable membrane that wraps the cell-scaffold composition. This semi-permeable membrane is permeable to small molecules and so allows diffusion of nutrients and oxygen and elimination of wastes; but this membrane is impermeable to macromolecules such as collagen and glycosaminoglycans. These macromolecules that form the natural extracellular matrix are then retained within the scaffold. This membrane also isolates the cell-matrix construct from the host environment and protects from inflammatory and immunological response of the host against the biopolymeric scaffold.

Various polymers and polymer blends can be used to manufacture this membrane, including but not limited to, polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), PTFE, as well as derivatives, copolymers and mixtures of the foregoing.

In one embodiment, the semi-permeable membrane is generated by polyelectrolyte complexation: polyanion (PA) and polycation (PC) via interactions between oppositely charged polymers form polyelectrolyte complex (PEC). The anionic component may be a biocompatible polymer, such as, but not limited to, sodium alginate, cellulose sulfate, carboxymethyl cellulose, or hyaluronic acid, and the cationic component may be made of a polymer, such as, but not limited to, chitosan, poly(L-lysine, poly(L-ornithine), Poly(methylen-co-guanidine), poly(vinylamine), poly(ethylenimine), poly (DADMAC), or poly(N-vinylpyrrolidone), for example.

To carry out the encapsulation of the cell-matrix construct with a semi-permeable PEC membrane, cell matrix-construct is first immersed in the anionic solution and then in the cationic solution. After a reaction time that varies depending on the nature of the anionic and cationic components, a mechanically stable semi-permeable membrane is formed. Depending on the reaction conditions (polymer concentration, reaction time), the scaffold is either tightly wrapped within the membrane or separated from it by a gap.

Volume $V_I$, is defined as the space that is outwardly limited by the internal semi-permeable membrane "I" and comprises the living core made of chondrocyte-like cells derived from HDFs, for example.

2. The External Membrane

The external membrane may be expandable, elastic and/or inflatable in order to be implanted through a minimally invasive posterior surgical procedure and when expanded to fit exactly the cavity of discectomy. This membrane is hermetic to fluid but permeable to oxygen and is filled with medium that provides nutrients and growth factors to the cells. The fluid enclosed within the envelop forms a fluid environment that transfers IHP to the living cells. When the patient stands up, he applies some load on his spine that is transferred to the living cells through the membrane that is filled with fluid. This membrane is mechanically resistant to support the load.

The external membrane may be made of a biocompatible, biodegradable polymer. Various polymers can be used to manufacture this membrane including, but not limited to, polyglycolic acid (PGA), polylactic acid (PLA), polylactic-co-glycolic acid (PLGA), poly-$\epsilon$-caprolactone (PCL) polyurethane (PU), polydioxanone (PDO), polyethylenes, poly(glycerol sebacate) (PGS) as well as derivatives, copolymers and mixtures of the foregoing. In one embodiment the membrane is comprised of an expandable, biocompatible, biodegradable polyurethane.

This membrane is in direct contact with the host-surrounding tissue and is biocompatible to avoid inflammatory reaction of the host. Different techniques can be used to improve the membrane biocompatibility such as, but not limited to, coating the membrane with hyaluronic acid.

IV. Cells Utilized in the Invention

In certain embodiments of the invention, any cell may be employed so long as the cell is capable of differentiating into a chondrocyte or chondrocyte-like cell. In specific embodiments, the cell is in fact a chondrocyte, although it may be derived from a stem cell (for example, mesenchymal stem cell), or a fibroblast cell, such as a dermal fibroblast, tendon fibroblast, ligament fibroblast, or synovial fibroblast. Autologous cells may be utilized, although in alternative embodiments allogeneic cells are employed; in specific embodiments, the allogeneic cells have been assayed for disease and are considered suitable for human transmission. In certain aspects of the invention the cell or cells are autologous, although in alternative embodiments the cells are allogeneic. In cases wherein the cells are not autologous, prior to use in the invention the cells may be processed by standard means in the art to remove potentially hazardous materials, pathogens, etc. In particular aspects, the cells may be transfected with one or more nucleic acids, such as transfected with a growth factor, including BMP-2 -4, -6, and/or -7, for example.

In particular aspects, chondrocyte-like differentiation of human dermal fibroblasts may be facilitated by employing one or more of the following: seeding cells in alginate; seeding cells in extracellular matrix proteins such as aggrecan or perlecan, hypoxic conditions (such as hypoxia or one or more hypoxia-mimicking agents, for example lactate, Desferrioxamine mesylate (DFX), cobalt chloride ($CoCl_2$), or nickel, for example); high density micromass culture; presence of one or more growth factors (including, for example, bone morphogenetic proteins (BMPs), including at least BMP-2; transforming growth factor beta (TGF-$\beta$); insulin growth factor one (IGF-I); and fibroblast growth factors (FGFs) and particularly basic fibroblast growth factor (bFGF) and FGF-2, platelet-derived growth factor (PDGF), cartilage-derived morphogenetic protein (CDMP)]; presence of ascorbic acid, dexamethasone, parathyroid hormone-related protein (PTHrP), hedgehog proteins: sonic hedgehog (SHH) and Indian hedgehog (IHH)). Culture under mechanical stress may be employed. High density micromass culture is a culture technique that mimics the cellular condensation stage that occurs during the onset of cartilage formation in the developing limb.

In particular aspects of the invention, human dermal fibroblasts are employed, at least because they can be non-invasively harvested, such as from a punch biopsy as little as about 3 mm in diameter (in specific embodiments) from skin, for example a circular biopsy skin specimen. Also, human dermal fibroblasts can expand easily in culture and can differentiate into chondrocyte-like cells under particular culture conditions.

In accordance with the invention, autologous HDFs are harvested from punch biopsy of skin tissue (6 mm) from the patient. In the laboratory, subcutaneous fat and deep dermis are dissected away with scissors. The remaining tissue is minced and incubated overnight in 0.25% trypsin at 4° C. Then, dermal and epidermal fragments are mechanically separated. The dermal fragments of the biopsy are minced and the pieces are used to initiate explant cultures. Fibroblasts harvested from the explants are grown in Dulbecco's MEM (DMEM) with 10% calf serum at 37° C. in 8% $CO_2$. These cells are expanded before being differentiated into chondrocytes, in particular aspects.

Some aspects may employ HDFs purchased commercially, such as from laboratories (such as Cascade Biologics). The cells can be adult HDFs or neonatal HDFs. Neonatal foreskin fibroblasts are a very convenient source of cells, for example. These cells are used commercially and are readily available and easy to grow.

V. Growing and Differentiating Cells into Chondrocytes or Chondrocyte-Like Cells Mechanical stress/strain are important factors for chondrogenesis. The present method uses one or more mechanical strains and, in particular embodiments, uses intermittent hydrostatic pressure (IHP) as inducer of chondrogenic differentiation of HDFs. IHP is known as a potent stimulus for induction and maintenance of the chondrocyte phenotype. Recent studies have demonstrated that IHP stimulates chondroinduction of murine embryonic fibroblasts cultured with BMP-2. IHP can also induce chondrogenic differentiation of HDFs. It is known that HDFs can differentiate into chondrocyte-like cells under low oxygen tension. Therefore, in accordance with an embodiment of the present invention, mechanical stress, especially IHP and shear fluid stress, induce chondrogenic differentiation of fibroblasts cultured in a three dimensional matrix and low oxygen tension, for example.

Mechanical stress can be performed in vitro, in vivo, ex vivo, in vitro followed by in vivo, or a combination thereof. In an embodiment, the differentiation will be initiated in vitro, and the chondrocyte-like, cells seeded in the matrix will be then implanted in vivo and continue to grow and differentiate. The inert structure is intended to provide a physiologic loading regimen to induce in vivo differentiation of HDFs, in specific aspects of the invention.

In specific aspects of the invention, cells are induced to undergo differentiation into chondrocytes or chondrocyte-like cells. Such differentiation may occur prior to in vivo delivery, such as on a scaffold, or subsequent to delivery in vivo. In specific embodiments, the cell is subjected to conditions to facilitate differentiation into chondrocytes. In a further specific embodiment, a condition comprises mechanical stress. Regulation of genes by mechanical forces has been studied extensively for vascular endothelial cells and chondrocytes that are obviously subjected to high fluid shear or pressure load. In specific embodiments of the invention, mechanical stress stimulates chondrogenic differentiation of HDFs. Such mechanical stress may be of any kind, although in specific embodiments it comprises hydrostatic pressure and/or fluid shear stress. In additional specific embodiments, the stress is constant or intermittent.

In the present invention, mechanical stress, especially cyclic hydrostatic pressure and shear fluid stress induce chondrogenic differentiation of fibroblasts seeded in a three dimensional matrix. The choice of the co-culture conditions to stimulate the chondrogenic differentiation of HDFs is based on data known in the art. Different exemplary factors such as high cell density culture, culture with BMP-2 and ascorbic acid, culture in low oxygen tension are known to stimulate chondrogenesis and are used solely as examples in the invention as co-factors in addition to the mechanical stress.

Chondrocytes from intervertebral discs are difficult to harvest. The autologous cells are obtained from the patient's disc and so requires an invasive procedure (back surgery) to perform a biopsy. If cells are harvested from a healthy disc, it jeopardizes the functioning of a normal disc. If cells are harvested from a damaged disc during the discectomy, it provides abnormal cells from a degenerated tissue. Moreover, chondrocytes are difficult to expand in culture because they de-differentiate. Chondrocytes from other cartilages such as the elastic cartilage from the ear is easy to harvest but produces only hyaline cartilage and not fibro-cartilage as in the disc. Stem cells that are usually used for tissue engineering also have some disadvantages, because they require a bone marrow biopsy. A large quantity of cells is needed for tissue engineering, and it is difficult to obtain a sufficient quantity of adult stem cells.

The rationale for using autologous HDFs as a means of cell sourcing follows from the following: 1) HDFs can be non-invasively harvested from a punch biopsy as little as a 3.0 mm diameter circular skin specimen, for example; 2) the risk of contamination from another donor (such as Hepatitis B Virus, Human Immunodeficiency Virus, Creutzfeldt-Jakob disease, etc.) does not exist; and 3) HDFs can expand easily in culture and differentiate into chondrocyte-like cells under particular culture conditions. Other fibroblast populations could be used, such as tendon or ligament, for example. In an embodiment, autologous fibroblasts are preferred.

The choice of the culture conditions to stimulate the chondrogenic differentiation of HDFs is based on data known in the art. Different factors support chondrogenesis, such as, for example, high cell density culture, culture with BMP-2 and ascorbic acid, and seeding cells in alginate matrix. In vitro growth and/or differentiation of the cells in the cells/scaffold composition may comprise at least two or more days prior to use in vivo. In certain cases, the cells may be checked or monitored to ensure that at least some of the cells are dividing. Cells that are not dividing and/or that are not affixed directly or indirectly to the scaffold may be removed.

In other embodiments, HDFs are embedded in hydrogel that in specific embodiments is a natural hydrogel such as collagen, hyaluronic acid (HA), a combination of collagen/HA, alginate, chitosan; a synthetic hydrogel such as poly(ethyleneoxide) (PEO), poly(vinyl alcohol) (PVA), poly(acrylic acid) (PAA), poly(propylene furmarate-co-ethylene glycol (P(PF-co-EG), and polypeptides, or other biodegradable polymers such as poly(L-lactic acid) (PLA), poly(glycolic acid) (PGA), poly-lactic-co-glycolic acid (PLGA); or a combination of any of these above mentioned polymers. A cyclic hydrostatic compression is then applied using any suitable in vitro bioreactor in the art.

VI. Methods of Repairing Damaged Cartilage

In certain embodiments, the invention includes methods of repairing any damaged cartilage, although in particular aspects the cartilage is in an intervertebral disc or any joint. Generally, for disc embodiments when an intervertebral disc must be removed from between two adjacent vertebrae, e.g. in the lumbar spine, it is less invasive to surgically proceed posteriorly from the back of the patient. This minimally invasive procedure allows one to proceed with the curettage of the inter-somatic space through a small aperture within the annulus (tenotomy) for removing the degenerated fragments of the disc's nucleus. As the annulus fenestration is small, the present invention provides an intervertebral construct that is slid through the aforementioned incision and then expanded into the room generated by the nucleus removal within the inter-somatic space. The removal of the damaged disc and the installation of the construct are performed in the same posterior approach.

As mentioned above, the inert structure is made of two expandable balloons "I" and "E". At the rest position, the two balloons "I" and "E" are flat, deformable, shaped and fit one another. Once the balloon "I" is inside the balloon "E", they are both installed into the intervertebral space through the annulus aperture, and then successively inflated so as to define two distinct Volumes ($V_E > V_I$) of shapes (spherical, cylindrical, conical, etc.) depending on the contour of the inter-vertebral cavity and the load sharing, for example.

In particular aspects, the first balloon to be filled is the internal balloon "I" regardless of the volume of the remaining cavity. Volume $V_I$ represents the core of the construct that receives and houses the living core. Once filed with the living core, the balloon "I" is hermetically sealed. That is, once the envelope "I" is placed into the envelope "E", both are positioned into the intervertebral space through the annulus aperture, and then successively inflated. "I" is the first to be instrumented with the implantation of the living core, and then sealed. Then, the external balloon "E" is inflated with the media solution until its volume $V_E$ gets a contour that mates with, or follows, the inner surface of the remaining part of the natural disc alter the curettage thereof. This inner surface of the remaining disc can be either the remainder of the nucleus tissue or the inner wall of the natural annulus, depending how extensive the curettage has been performed.

In a second embodiment to install the intervertebral construct, "E" is positioned into the intervertebral space, then "I" is placed into "E", and they are both filled successively as aforementioned. In a third embodiment, "E" is positioned into the discectomy cavity, then the pre-encapsulated living core is placed into "E", and then "E" is filled with the media.

The volume of the cavity resulting from the discectomy may be evaluated prior to the installation of the external balloon "E" such that proper fluid volume can be selected and injected. The cavity volume could be, for instance, measured by introducing a fluid (e.g., water) therein, until the cavity is filled therewith, and by then withdrawing the fluid from the cavity by way of a syringe, thereby substantially exactly measuring the cavity's volume.

In certain aspects, the inert structure composition depends on the choice of tissue engineering system that relies on material of fabrication, pore characteristics, absorbability and mechanical properties, for example, such as non-degradable polymers, degradable polymers or naturally derived hydrogels (for example collagen, fibrin, agarose, alginate, etc.).

The living core or compartment ($V_I$) is made of chondrocyte-like cells derived from autologous Human Dermal Fibroblasts (HDFs), for example, such as those harvested from skin of the patient and seeded in a scaffold (such as alginate beads, or micofluidic scaffold, or any other polymeric scaffold) and fed from the supportive compartment ($V_E$). The advantage of this hybrid construct combining both an inert biomaterial acting as a nutrients delivery system and living cells easily harvested from skin is that it is capable of self maintenance or remodeling and may restore the disc function using a minimally invasive posterior surgical approach. Volume $V_E$, is defined as the space that separates layer "E" from layer "I" that comprises nutrients and growth factors (media) to be delivered to the cells (delivery system). This volume can be the result either of its filling by the liquid media, or its swelling from its wall (expandable hydrophilic biomaterial as hydrogel, for instance) after having been hydrated (the media is made of a high ratio of water).

Growth factors may be delivered through the semi-permeable internal membrane "I". Example of growth factors include, for example, cartilage-derived morphogenetic protein (CDMP), bone morphogenetic proteins (BMPs), transforming growth factor beta (TGF-β), and insulin growth factor one (IGF-I), fibroblast growth factors (FGFs), platelet-derived growth factor (PDGF), for example.

Mechanical strain, such as high fluid shear and/or pressure load, is transferred on internal layer "I", and therefore on $V_I$ through the external layer "E" and the external area $V_E$. This mechanical strain induces chondrogenic differentiation of the cells inside the internal layer.

The draining system is then installed, wherein each catheter exiting from the intervertebral space through the tenotomy aperture is carefully kept away from the adjacent root, or at least positioned along the root without any harmful conflict.

A trans-muscular path is performed using an introducer from the operative site to a subcutaneous location distant from the skin aperture. Each tube is "tunnelized" into the aforementioned muscular path then connected to the corresponding reservoir. The two reservoirs are distant from the medial skin incision, positioned at 2 or 3 centimeters from the medial line, subcutaneously placed so that they are easily palpable and identifiable. Each skin incision is closed.

As it is usual to proceed after such minimally invasive posterior approach, the patient is asked to stand up as early as the day after the surgery, and can begin to walk again. Therefore, the implant receives the right cyclic hydrostatic pressure regimen under physiological load, which is critical for HDFs growth and conversion.

Periodically, such as one or more times per week or month, the media may be changed The draining system allows one to provide the volume $V_E$ with the appropriate amount of new media in order to continue to supply the living core, but also to maintain the adequate volume and therefore the right pressure regimen. The individual lies face-down. Each reservoir is simultaneously punctured with a needle. A syringe is plugged in on each of these needles and the new media is slowly injected by pushing down the piston while the same amount of fluid is simultaneously removed from the other syringe by pulling up, so that the internal pressure remains almost the same, and avoids the volume $V_E$ to collapse, or, at the contrary, to deliver too high of a pressure to the volume $V_I$, which could cause irreversible damage to the living core. The procedure is stopped when the color and the aspect of the exiting fluid has become identical to the entering fluid, for example. Samples from the removed used media may be taken for bacteriological, pathological and chemical purposes.

When the living core is capable of self maintenance and has filled the room of the discectomy, both tubes and reservoirs can be removed. Alternatively, only one or both reservoirs can be removed under local anesthesia while the tubes are tied at their distal end. In another alternative embodiment, both can be let in place.

In specific embodiments, a follow-up MRI is performed, such as within weeks or months of the surgery (for example, about 6 weeks after surgery) to assess the graft growth and to document the disc healing.

In another embodiment, the engineered living core is pre-encapsulated and released as aforementioned.

These foregoing functions are provided by the inert structure of the invention that relies on two concentric membranes with two different skills. The external envelop is mechanically able to maintain disc height under loading; is inflatable (in order to be implanted through a minimally invasive posterior approach and receive the media solution); is resilient (to transfer load sharing onto the graft); is expandable (to allow its swelling and fill the cavity resulting of the discectomy); is hermetic (to avoid any leak of the media, extrusion of scar tissues into the spinal canal, or recidivism of herniation through the annulus defect—tenotomy—); is biodegradable (the envelop resorbs to allow the graft to reconnect with the natural remaining disc); and is biocompatible (to minimize inflammatory reaction). It may be drained with one or several catheter(s) connected to one or several Rickham reservoir(s) subcutaneously inserted at the end of the surgical procedure, for example.

These reservoirs are intended to remove any toxic wastes accumulated with the metabolism (free radicals or lactic acid, for example), as well as any other cellular scraps consecutive to the growth. They also allow providing the volume $V_E$ with the appropriate amount of new media in order to continue to supply the living core, but also to maintain the adequate volume and therefore the right pressure regimen. They are removed when the living core is capable of self maintenance and has filed the room of the discectomy.

It should be noted that the various components and features of the hybrid structure, as well as the method of repairing damaged cartilage and method for growing HDFs into chondrocyte-like cells described above, can be combined in a variety of ways so as to provide other embodiments within the scope of the invention.

VII. Alternative Embodiment of the Invention

In another embodiment, instead of having two generally spherically (for example) concentric envelopes, the device could be made of a unique external envelope "E" with the same aforementioned characteristics (especially expandability and/or inflatable properties), and receives an unwrapped living core (non-encapsulated nor wrapped up with a membrane). Actually, in this embodiment, this living core is a cell matrix construct and is directly positioned into "E". Then, the volume $V_E$ is expanded with the media liquid solution until mating the cavity.

Thus, in another embodiment, instead of having two "concentric" balloons, the device is comprised of a unique external balloon "E" with the same aforementioned characteristics (especially expandability and/or inflatable properties) for housing the engineered living core. Once the living core is released within the membrane "E", the volume $V_E$ is expanded with the media liquid solution until the membrane "E" reaches the boundaries of the cavity. Neither barrier nor membrane wrap up the graft anymore. While the media is consumed, the living core expands to the inner wall of the balloon/layer/membrane "E". The envelop resorbs and the graft reconnects with the natural remaining disc.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

Exemplary embodiments of materials and methods for use in the invention are described in this Example.

Cell Culture

While autologous HDFs harvested from the patient are used to construct the implant, preliminary studies are performed using neonatal foreskin fibroblasts, as there are convenient sources of cells for experimental purpose, for example. Further studies using autologous cells harvested from the patient are performed to demonstrate that the procedure works with these cells.

Neonatal foreskin HDFs are obtained from Cascade Biologics (Portland, Oreg.) and expanded in vitro with DMEM (Invitrogen, Carlsbad, Calif., USA), containing 10% FBS (Invitrogen) and antibiotics. Suspensions of HDFs are seeded in alginate or in monolayer culture as described below.

To generate alginate gel cultures, cells are suspended at high density ($10^7$ cells/ml) in 2% wt/vol medium viscosity alginate (Sigma-Aldrich, St. Louis, Mo.), and 25 mL droplets are crosslinked in 100 mM $CaCl_2$, 0.9% NaCl solution. The resulting alginate beads are then washed extensively in DMEM containing 10% FBS and antibiotics. Alginate beads are immersed in DMEM containing 10% FBS and antibiotic supplemented with 100 ng/ml recombinant human Bone Morphogenic Protein-2 (BMP-2) and 50 mg ascorbic acid. Such conditions: high cell density and culture with BMP-2 and ascorbic acid have been chosen because they are known to stimulate chondroinduction (Watt, 1988; Dozin et al., 1992; Sullivan et al., 1994; Denker et al., 1999; Zur Nieden et al., 2005; Zhou et al., 2004).

To generate monolayer cultures, HDFs are seeded in plastic flasks with an oxygen level of 20% in DMEM containing 10% FBS without BMP-2 and without ascorbic acid. These cells serve as control.

Culture Under 5% and 20% $O_2$

Cell-embedded alginate beads are kept under an atmosphere of 5% $O_2$, 5% $CO_2$, and 90% $N_2$ in an $O_2$-/$CO_2$-regulated incubator (low oxygen tension) or under 20% $O_2$, 5% $CO_2$, and 75% $N_2$ in an $CO_2$-regulated incubator (atmospheric oxygen tension) and cultured for 3 weeks. Then, assessment of chondrogenic differentiation is performed (see Example 3, for example).

Hydrostatic Compression

Cell-embedded alginate beads are divided into pressurized and control groups, and those from each group placed in separate flexible polyethylene/nylon bags permeable to oxygen and carbon dioxide. The bags are filled with 15 ml of medium and are heat-sealed to exclude all air.

The bags in the pressurized group are placed within a newly developed device designed for the application of cyclic hydrostatic compression (Elder et al., 2005). This device allows the comparison of loading regimes in a wide physiologic range under an equal three-dimensional culture conditions. It consists of a large cylindrical stainless steel base connected to a lid by bolts that compress an intervening o-ring. A hydraulic cylinder is welded to the lid so that its interior is continuous with that of the chamber. The cylinder and chamber are completely filled with water, so that rapid hydrostatic compression is achieved by a force (generated by a MTS servohydraulic testing machine) applied to the cylinder's piston. A stable 37° C. is maintained by immersing the chamber in a temperature-regulated circulating water bath. Bags in the control group are placed in a separate, water-filled stainless steel chamber in the same water bath.

The magnitude and frequency of the applied pressure are chosen to be within the physiological ranges (Mow et al., 1992) that have previously been demonstrated to stimulate chondrogenic differentiation of multipotential mesenchymal cells (Elder et al., 2005) and redifferentiation of dedifferentiated chondrocytes (Domm et al., 2000). Short and long duration pressurization are tested and a successful chondroinductive hydrostatic pressurization model is determined between the short and long duration hydrostatic pressurization by quantitative and qualitative assessment of chondrogenesis.

An exemplary regimen comprises the following:

1.0 Hz sinusoidal hydrostatic compression waveform with a minimum applied pressure of 0.3 MPa and a maximum 5.0 MPa. For short duration pressurization, the cells are pressurized 1 h/day for 7 days. For long duration pressurization, the cells are pressurized 4 h/day for 7 days. Each day, immediately upon completion of loading, cultures are removed from the pressure vessel and returned to a water bath inside the tissue culture incubator.

Cell viability and chondrogenic differentiation of HDFs under hydrostatic cyclic compression and cultured under specific conditions (such as hypoxia, chondrogenic medium, high cell density) are assessed using techniques standard in the art.

In another embodiment, the conversion of fibroblast cells into chondrocytes is induced by hydrostatic cyclic pressure and shear stress. In this case, the cells are seeded into a microfluidic scaffold.

Assessment of chondrogenic differentiation is performed (see Example 3, for example).

Example 2

Assessment of Cell Viability of HDFs in Alginate Beads

The viability of HDFs in alginate beads cultured in chondrogenic medium is tested by light microscopy and/or viability test, in specific aspects of the invention. Light microscopy is employed to study morphology and proliferation of HDFs. In an exemplary viability test, alginate beads are dissolved in dissolving-buffer (0.55 M Na-Citrate, 1.5 M NaCl, and 0.5 M EDTA), cells are centrifuged, and the pellet is treated with collagenase for 1 h. Cells are resuspended in DMEM, and viability is determined using a Neubauer chamber and the trypan blue exclusion method, for example.

Example 3

Assessment of Chondrogenic Differentiation

In specific embodiments, HDFs are characterized by the production of collagen of type I, III and V, while chondrocytes are characterized by the production of collagen of type II, IX, XI and the production of sulfated proteoglycans.

Chondrogenic differentiation is assessed by measuring sulfated glycosaminoglycan (sGAG) content and collagen I et II production by western blotting. The rate of collagen synthesis is measured by [$^3$H]-proline incorporation.

Total DNA and sGAG Content

Cells in alginate beads are recovered from the alginate using 55 mM sodium citrate, 0.9% NaCl solution. Then the cells are lysed in 300 μl of 0.5% v/v Nonidet P-40 buffer (50 mM Tris-Cl, 100 mM NaCl, 5 mM $MgCl_2$). The lysate is transferred to microcentrifuge tubes, spun, and DNA is measured in a 100 μl supernatant aliquot using the Hoescht dye method (DNA Quantification Kit, Sigma, St. Louis, Mo.) with calf thymus DNA as standard. The remaining lysis buffer is removed and sGAG digested in 100 μl of 2% v/v papain, 20 mM sodium acetate (pH 6) overnight at 60° C. Total sGAG content is then measured by the dimethylmethylene blue precipitation method (Blyscan Glycoaminoglycan Assay, Biocolor, Ltd.) using chondroitin 4-sulfate purified from bovine trachea as standard. For each sample, the sGAG content is normalized to the DNA content.

Western Blot for Collagen Type I and Type II

Five beads of each sample are dissolved in 400 ml buffer (55 mM sodium citrate, 150 mM NaCl). For collagen solubilization, 100 μl of 0.25 M acetic acid and 100 μl pepsin solution (1 mg/ml 50 mM acetic acid: P-6887, Sigma) are added and the mixture kept at 4° C. for 24 h. Then, 100 μl of a 10× stock solution TBS (1 M Tris, 2M NaCl and 50 mM $CaCl_2$, pH 8) and 100 ml pancreatic elastase (1 mg/ml TBS; Sigma E-6883) are added and samples incubated for 30 min at 37° C. The samples are centrifuged for 10 min at 9000×g. The supernatant is collected. 25 μl of bovine collagen type I, bovine collagen type II (Sigma) or sample (each containing 5 mg total protein; quantification with Bio-Rad protein assay) are mixed with 6 μl sample buffer, denatured for 5 min at 95° C., and loaded on a 7% acrylamide gel. Electrophoresis is performed. Gel is transferred onto the blotting membrane. The membrane is blocked overnight in blocking-buffer (10% milk powder in TBST buffer) and then incubated with a mouse monoclonal antibody anti-collagen type I antibody (COL-1, ab 6308, Abcam Inc) or a mouse monoclonal anti-body anti-collagen type II (5B2.5, ab3092, Abcam Inc) overnight at 4° C. The membrane is washed with TBST buffer. The goat antimouse biotin conjugated secondary antibody is added (1:500) for 1 h followed by streptavidin-HRP at 1:1000 dilution for 1 h. Blot is developed using ECL from Amersham.

Measure of [$^3$H]-Proline Incorporation

In alginate beads in which the rate of collagen production is determined, the medium is removed and replaced with DMEM supplemented with 10% FBS, antibiotics, 25 mg ascorbic acid, [$^3$H] proline at 10 μCi/ml, and 100 μg/ml β-amino-propionitrile (β-APN) to inhibit collagen cross-link formation. After a 24 h incubation period, the incorporation of [$^3$H] proline into collagen is measured. Beads are digested at 65° C. overnight in 1 ml papain solution [0.125 mg/ml (2.125 units/ml, Sigma), 0.1 M $Na_2HPO_4$, 0.01 M EDTA, pH 6.5]. 200 ml of each sample are added to 2 ml of scintillation fluid and measured using a scintillation counter.

500 μl of each sample is mixed with 500 μl PBS and used to determine the DNA content. Samples and blanks (containing 1 ml PBS) are treated with an ultrasonic beam for 15 s. 0.5 ml of RNAse and 0.5 ml pronase are added and incubated at 37° C. for 30 min. Then, 0.5 ml of ethidium bromide is added, samples are incubated for 30 min, and they are measured with a fluorometer.

[$^3$H]-proline incorporation is normalized to total DNA content.

Example 4

Exemplary Design of Studies

In specific aspects of the invention, cell viability and chondrogenic differentiation of HDFs seeded are determined in three-dimensional alginate bead cultures. In particular, cell viability and chondrogenic differentiation of HDFs seeded in alginate beads and cultured in a chondrogenic medium (medium supplemented with BMP-2 and ascorbic acid) under 20% $O_2$ are compared to HDFs in monolayer cultures in DMEM with 10% FBS under 20% $O_2$ using the exemplary method described above.

In another aspect of the invention, the effects of oxygen tension on the differentiation of HDFs cultured in alginate beads is determined. HDFs seeded in alginate beads in the chondrogenic medium are cultured for 3 weeks in 2 different oxygen tension: 1) low oxygen tension of 5% $O_2$, 5% $CO_2$, and 90% $N_2$ in an $O_2$-/$CO_2$-regulated incubator; and 2) atmospheric oxygen tension of 20% $O_2$, 5% $CO_2$, and 75% $N_9$ in an $CO_2$-regulated incubator.

Chondrogenic differentiation is compared using the exemplary method described above.

In an additional embodiment of the invention, the effects of hydrostatic compression on the differentiation of HDFs cultured in alginate beads are determined. HDFs seeded in alginate beads in the chondrogenic medium are subjected to different stimuli: 1) 1 h/day for 7 days hydrostatic pressure (1.0 Hz sinusoidal hydrostatic compression min 0.3 MPa max 5.0 Mpa) and 20% $O_2$; 2) 4 h/day for 7 days hydrostatic pressure (1.0 Hz sinusoidal hydrostatic compression min 0.3 MPa max 5.0 Mpa) and 20% $O_2$; 3) 1 h/day for 7 days hydrostatic pressure (1.0 Hz sinusoidal hydrostatic compression min 0.3 MPa max 5.0 Mpa) and 5% $O_2$; 4 h/day for 7 days hydrostatic pressure (1.0 Hz sinusoidal hydrostatic compression min 0.3 MPa max 5.0 Mpa) and 5% $O_2$.

Chondrogenic differentiation may be assessed using the exemplary method described above.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PATENTS

U.S. Pat. No. 6,489,165
U.S. Pat. No. 6,627,422

PUBLICATIONS

Barry F, Boyton R E, Liu B et al. Chondrogenic differentiation of mesenchymal stem cells from bone marrow: differentiation-dependent gene expression of matrix components. Exp Cell Res 2001 (268):189-200.

Carter D R, Orr T E, Fyhrie D P, Schurman D J. Influences of mechanical stress on prenatal and postnatal skeletal development. Clin Orthop 1987(219):237-250.

Cui, L., Yin, S., Deng, C L., Yang, G H., Chen, F G., Liu, W., Liu, D L., Cao, Y L. Cartilage-derived morphogenetic protein 1 initiates chondrogenic differentiation of human dermal fibroblasts in vitro. Zhonghua Yi Xue Za Zhi. 2004 Aug. 2; 84(15):1304-1309.

Denker A E, Haas A R, Nicoll S B, Tuan R S. Chondrogenic differentiation of murine C3H10T1/2 multipotential mesenchymal cells: I. Stimulation by bone morphogenic protein-2 in high-density micromass cultures Differentiation 1999; 64:67-76

Domm C, Fay J, Schunke M, Kurz B. Redifferentiation of dedifferentiated joint cartilage cells in alginate culture. Effect of intermittent hydrostatic pressure and low oxygen partial pressure Orthopade February 2000; 29(2):91-99

Dozin, R. Quarto, G: Campanile & R. Cancedda: In vitro differentiation of mouse embryo chondrocytes: requirement for ascorbic acid. Eur J Cell Biol 1992; 58, 390-4

Elder S H, Fulzele K S, McCulley W R. Cyclic hydrostatic compression stimulates chondroinduction of C3H/10T1/2 cells. Biomechan Model Mechanobiol 2005(3): 141-146

French M M, Rose S, Canseco J and Athanasiou K A. Chondrogenic differentiation of adult dermal fibroblasts. Annals of Biomedical Engineering 2004; 32 (1):50-56.

Hauselmann H J, Aydelotte M B, Schumacher B L, Kuettner K E, Gitelis S H, Thonar E J. Synthesis and turnover of proteoglycans by human and bovine adult articular chondrocytes cultured in alginate beads. Matrix 1992(12):116-129.

Kessler, D., Dethlefsen, S., Haase, I., Plomann, M., Hirche, F., Krieg, T., Eckes, B. Fibroblasts in mechanically stressed collagen lattices assume a "synthetic" phenotype. J. Biol. Chem. September 2001; 276(39):36575-36585.

Majumdar M K, Wang E and Morris E A. BMP-2 and BMP-9 promotes chondrogenic differentiation of human multipotential mesenchymal cells and overcomes the inhibitory effect of IL-1. J. Cell. Physiol. 2001(189):275-284.

Meisel, H J., Alasevic, O., Hutton, W., Ganey, T. Disc repair with autologous chondrocytes: A pilot clinical study. European Cells and Materials. Vol. 10 Suppl. 3, 2005 (page 39)

Watt F M. Effect of seeding density on stability of the dedifferentiated phenotype of pig articular chondrocytes in culture. J Cell Sci 1988; 89:373-378.

Mizuno H, Roy A K, Vacanti C A, Kojima K, Ueda M, and Bonassar L J. Tissue-engineered composites of annulus fibrosus and nucleus pulposus for intervertebral disc replacement. Spine 2004 (29):1290-1298.

Mow V C, Ratcliffe A, Poole A R. Cartilage and diarthrodial joints as paradigms for hierarchical materials and structures. Biomaterials 1992; 13(2):67-97.

Nicoll S B., Wedrychowska, A., Smith, N R., Bhatnagar, R S. Modulation of proteoglycan and collagen profiles in human dermal fibroblasts by high density micromass culture and treatment with lactic acid suggests change to a chondrogenic phenotype. Connect. Tissue Res. 2001; 42(1):59-69.

T. A. Sullivan, B. Uschmann, R. Hough & P. S. Leboy: Ascorbate modulation of chondrocyte gene expression is independent of its role in collagen secretion. J Biol Chem 1994; 36, 22500-6

Watt F M. Effect of seeding density on stability of the dedifferentiated phenotype of pig articular chondrocytes in culture. J Cell Sci 1988; 89:373-378

Zhou S, Glowacki J, and Yates K E. Comparison of TGF-b/BMP pathways signaled by demineralized bone powder and BMP-2 in human dermal fibroblasts. J Bone Miner Res 2004; 19:1732-1741.

Zur Nieden N I, Kempka G, Rancourt D E, Ahr H J. Induction of chondro-, osteo- and adipogenesis in embryonic stem cells by bone morphogenic protein-2: effect of cofactors on differentiating lineages. BMC Dev Biol, 2005; Jan. 26 (5):1-15

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method of repairing damaged cartilage in a joint of an individual, comprising delivering a device to the respective joint of the individual, wherein the device comprises:
   cells/scaffold composition; and
   an encapsulating device that comprises:
      a first membrane having an inside and an outside;
      a second membrane having an inside and an outside, wherein the first membrane is encapsulated inside the second membrane;
      a first volume disposed inside the first membrane;
      a second volume that is disposed outside the first membrane and that is disposed inside the second membrane; and
      a structure for adding fluid to the second volume, removing fluid from the second volume, or both,
      wherein the cells/scaffold composition is disposed inside the first membrane and the first membrane has the following characteristics:
         semi-permeable;
         biocompatible;
         biodegradable; and
         resorbable,
      wherein the second membrane has the following characteristics:
         biocompatible;
         hermetic to fluid;
         permeable to oxygen;
         resorbable;
         biodegradable; and
         expandable.

2. The method of claim 1, wherein the method further comprises preparing the cells/scaffold composition under suitable ex vivo conditions.

3. The method of claim 2, wherein preparing the cells/scaffold composition is defined as subjecting one or more cells to a scaffold under suitable conditions.

4. The method of claim 2, wherein the method further comprises preparing the cells/scaffold composition for no less than about two to three days.

5. The method of claim 2, wherein the suitable conditions allow proliferation of the cells.

6. The method of claim 2, wherein the suitable conditions allow the stimulation of chondrogenic differentiation.

7. The method of claim 2, wherein the suitable conditions are further defined as being under high density micromass culture, being under low oxygen tension (between about 1.0%-7.5%), being under mechanical stress, and/or being fed by a medium supplemented with growth factors, ascorbic acid, and/or dexamethasone.

8. The method of claim 1, wherein the cells are chondrocytes or chondrocyte-like cells derived from fibroblasts or stem cells.

9. The method of claim 8, wherein the fibroblasts cells are dermal fibroblasts, tendon fibroblasts, ligament fibroblasts, synovial fibroblasts, or foreskin fibroblasts.

10. The method of claim 8, wherein the fibroblasts are dermal fibroblasts.

11. The method of claim 1, wherein the cells/scaffold composition is subjected to mechanical stress.

12. The method of claim 11, wherein the mechanical stress is defined as hydrostatic pressure, fluid shear stress, or a combination thereof.

13. The method of claim 11, wherein the mechanical stress is intermittent.

14. The method of claim 11, wherein the mechanical stress is fluid shear stress and the scaffold is microfluidic scaffold.

15. The method of claim 1, wherein the delivering step is defined as implanting the device using minimally invasive surgery.

16. The method of claim 1, wherein following implantation of the device into the individual, the second membrane is inflated to fill a void in the joint.

17. The method of claim 1, wherein the joint is an intervertebral disc and wherein prior to delivery of the device to the intervertebral disc of the individual, at least part of an endogenous intervertebral disc was removed from the individual.

18. The method of claim 1, wherein the joint is an intervertebral disc, a knee, a shoulder, an elbow, a hip, or a temporo-mandibular joint.

19. The method of claim 1, wherein at least part of the second volume is exchanged.

20. The method of claim 1, wherein the structure of the device comprises:
a first tube having first and second ends, said first end of the first tube disposed within the second volume;
a second tube having first and second ends, said first end of the second tube disposed within the second volume;
a first reservoir; and
a second reservoir,
wherein following delivery of the device to an intervertebral disc in the individual and following inflation of the second membrane, the second ends of the first and second tubes are respectively connected to the first and second reservoirs.

21. The method of claim 20, wherein the first and second reservoirs are subcutaneously positioned in the individual.

22. The method of claim 20, further comprising removing at least part of the second volume through the first reservoir.

23. The method of claim 20, further comprising removing fluid from the first or second reservoir, delivering a fluid to the respective second or first reservoir, or concomitantly removing fluid from the first or second reservoir and delivering a fluid to the respective second or first reservoir.

24. The method of claim 20, wherein the cells/scaffold composition is inserted into the first membrane prior to delivery of the device into the individual or wherein the cells/scaffold composition is inserted into the first membrane subsequent to delivery of the device into the individual.

25. The method of claim 20, wherein the first membrane is inserted into the second membrane prior to delivery of the device into the individual or wherein the first membrane is inserted into the second membrane subsequent to delivery of the device into the individual.

26. The method of claim 1, further comprising sealing the first membrane, sealing the second membrane, or both.

27. The method of claim 1, wherein the scaffold is comprised of a synthetic polymer, a natural hydrogel, or a synthetic hydrogel.

28. The method of claim 27, wherein the synthetic polymer is polyglycolic acid, polylactic acid, polylactic-co-glycolic acid, poly-$\epsilon$-caprolactone, or poly(glycerol-Sebacate) (PGS).

29. The method of claim 27, wherein the synthetic polymer is a polyphosphazene, a polyanhydride, or a poly(orthoester).

30. The method of claim 27, wherein the natural hydrogel comprises collagen, hyaluronic acid, alginate, agarose, chitosan, fibrin, gelatin, or a copolymer thereof.

31. The method of claim 27, wherein the synthetic hydrogel comprises poly(ethylene oxide), poly(vinyl alcohol), poly (acrylic acid), poly(propylene fumarate-co-ethylene glycol), or a copolymer thereof.

32. The method of claim 1, wherein the cells are chondrocyte cells or chondrocyte-like cells.

33. The method of claim 1, wherein the chondrocyte cells or chondrocyte-like cells secrete a molecule selected from the group consisting of aggrecan, type II collagen, Sox-9 protein, cartilage link protein, and perlecan.

34. The method of claim 1, wherein the cells were differentiated from fibroblast cells and/or stem cells.

35. The method of claim 34, wherein the fibroblast cells are dermal fibroblasts, tendon fibroblasts, ligament fibroblasts, synovial fibroblasts, foreskin fibroblasts, or a mixture thereof.

36. The method of claim 1, wherein the first membrane is comprised of a biodegradable, biocompatible, and resorbable polymer.

37. The method of claim 1, wherein the first membrane is comprised of a polyacrylate, a polyvinylidene, a polyvinyl chloride copolymer, a polyurethane, a polystyrene, a polyamide, a cellulose acetate, a cellulose nitrate, a polysulfone, a polyphosphazene, a polyacrylonitrile, a poly(acrylonitrile/ covinyl chloride) or a derivative, copolymer or mixture thereof.

38. The method of claim 1, wherein the first membrane is generated by polyelectrolyte complexation.

39. The method of claim 1, wherein the second membrane is comprised of polyglycolic acid (PGA), polylactic acid (PLA), polylactic-co-glycolic acid (PLGA), poly-$\epsilon$-caprolactone (PCL), polyurethane (PU), polydioxanone (PDO), a polyethylene, poly (glycerol sebacate) (PGS), or a derivative, copolymer, or mixture thereof.

40. The method of claim 1, wherein the rate of resorbability of the second membrane is slower than the rate of resorbability of the first membrane.

41. The method of claim 1, wherein the implantable device comprises one or more nutrients, growth factors, and/or medicaments.

42. The method of claim 41, wherein the device is further defined as comprising a basal cell culture medium comprising the one or more nutrients, growth factors, and/or medicaments.

43. The method of claim 42, wherein the medium is supplemented with Fetal Bovine Serum (FBS), ascorbic acid, and/or dexamethasone.

44. The method of claim 41, wherein the nutrients, growth factors, and/or medicaments are present in the scaffold, the first volume, the second volume, or a combination thereof.

45. The method of claim 41, wherein the growth factor is selected from the group consisting of bone morphogenetic protein 2 (BMP-2), BMP-4, BMP-6, BMP-7, cartilage-derived morphogenetic protein (CDMP), transforming growth factor beta (TGF-β), insulin growth factor one (IGF-I), fibroblast growth factors (FGFs), basic fibroblast growth factor (bFGF), FGF-2, platelet-derived growth factor (PDGF), and a mixture thereof.

46. The method of claim 41, wherein the medicament is further defined as one or more of an antibiotic, antifungal agent, or antiviral agent.

47. The method of claim 1, wherein the structure comprises one or more tubes.

48. The method of claim 1, wherein the structure comprises one or more catheters and/or one or more reservoirs.

49. The method of claim 1, wherein the structure is further defined as comprising one or more of:
   a first tube;
   a second tube;
   optionally, a first reservoir; and
   optionally, a second reservoir.

50. The method of claim 49, wherein the first and second tubes respectively comprise first ends positioned within the second volume, wherein the first and second tubes respectively comprise second ends connected to first and second reservoirs, or both.

51. The method of claim 49, wherein the first and/or second tubes are comprised of the same material as the second membrane.

52. The method of claim 49, wherein the first and/or second tubes are comprised of silicone rubber.

* * * * *